(12) United States Patent
Kawabata et al.

(10) Patent No.: US 9,078,594 B2
(45) Date of Patent: Jul. 14, 2015

(54) ULTRASOUND DIAGNOSTIC AND TREATMENT DEVICE

(75) Inventors: Kenichi Kawabata, Kodaira (JP); Rei Asami, Kawasaki (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 13/639,109

(22) PCT Filed: Apr. 5, 2011

(86) PCT No.: PCT/JP2011/058568
§ 371 (c)(1),
(2), (4) Date: Nov. 7, 2012

(87) PCT Pub. No.: WO2011/125991
PCT Pub. Date: Oct. 13, 2011

(65) Prior Publication Data
US 2013/0053691 A1 Feb. 28, 2013

(30) Foreign Application Priority Data
Apr. 9, 2010 (JP) .................................. 2010-090261

(51) Int. Cl.
*A61B 8/00* (2006.01)
*A61B 8/08* (2006.01)
(Continued)

(52) U.S. Cl.
CPC ... *A61B 8/08* (2013.01); *A61B 8/13* (2013.01); *A61B 8/481* (2013.01); *A61N 7/02* (2013.01);
(Continued)

(58) Field of Classification Search
CPC ........... A61B 8/08; A61B 2017/00106; A61B 2019/5276; A61B 8/13; A61B 8/481; A61B 2503/40; A61N 7/02; A61N 2007/0039; A61N 2007/0052; A61N 2007/0065; A61N 2007/027

USPC ................................................... 600/437–469
See application file for complete search history.

(56) References Cited

U.S. PATENT DOCUMENTS 5,585,112 A * 12/1996 Unger et al. .................. 424/450
5,853,752 A * 12/1998 Unger et al. .................. 424/450
(Continued)

FOREIGN PATENT DOCUMENTS

JP 2006-320405 11/2006
JP 2007-7279 1/2007
(Continued)

OTHER PUBLICATIONS

JP Office Action for JP Patent Application No. 2012-509659, issued on Sep. 10, 2013.
(Continued)

*Primary Examiner* — Sanjay Cattungal
(74) *Attorney, Agent, or Firm* — Baker Botts L.L.P.

(57) ABSTRACT

Provided is an ultrasound diagnostic and treatment device for tumors which is used in combination with a phase-shift ultrasound contrast agent. By using a phase-shift ultrasound contrast agent, irradiating phase-shift ultrasonic waves from a phase-shift ultrasonic wave transmitter (18), irradiating ultrasonic waves for holding microbubbles from an ultrasonic wave transmitter (29) for holding microbubbles, and using a phase-shift detecting ultrasonic wave transceiver (19) to observe the phase shift, the ultrasound diagnostic and treatment device generates and holds the microbubbles in advance on the entire site (16) requiring treatment, and irradiates ultrasonic waves for treatment having a moderate intensity of 1 kW/cm$^2$ or lower on the entire site (16) requiring treatment with the microbubbles as the target from a ultrasonic wave transmitter (20) for treatment.

20 Claims, 20 Drawing Sheets

(51) Int. Cl.
*A61N 7/02* (2006.01)
*A61B 8/13* (2006.01)
*A61B 17/00* (2006.01)
*A61B 19/00* (2006.01)
*A61N 7/00* (2006.01)

(52) U.S. Cl.
CPC .............. *A61B 2017/00106* (2013.01); *A61B 2019/5276* (2013.01); *A61B 2503/40* (2013.01); *A61N 2007/0039* (2013.01); *A61N 2007/0052* (2013.01); *A61N 2007/0065* (2013.01); *A61N 2007/027* (2013.01)

(56) References Cited

U.S. PATENT DOCUMENTS

| | | | |
|---|---|---|---|
| 5,935,553 A * | 8/1999 | Unger et al. | 424/9.51 |
| 6,071,495 A * | 6/2000 | Unger et al. | 424/9.51 |
| 6,443,898 B1 * | 9/2002 | Unger et al. | 600/458 |
| 6,896,659 B2 * | 5/2005 | Conston et al. | 600/458 |
| 7,078,015 B2 * | 7/2006 | Unger | 424/9.52 |
| 7,470,241 B2 * | 12/2008 | Weng et al. | 601/3 |
| 8,057,408 B2 * | 11/2011 | Cain et al. | 601/2 |
| 2002/0151792 A1 * | 10/2002 | Conston et al. | 600/439 |
| 2003/0039613 A1 * | 2/2003 | Unger et al. | 424/9.51 |
| 2005/0163716 A1 * | 7/2005 | Unger et al. | 424/9.52 |
| 2005/0283098 A1 * | 12/2005 | Conston et al. | 601/2 |
| 2006/0264809 A1 * | 11/2006 | Hansmann et al. | 604/22 |
| 2007/0016042 A1 | 1/2007 | Kawabata et al. | |
| 2007/0038099 A1 | 2/2007 | Sugita et al. | |
| 2007/0083120 A1 * | 4/2007 | Cain et al. | 600/439 |
| 2008/0319356 A1 * | 12/2008 | Cain et al. | 601/2 |
| 2009/0036774 A1 * | 2/2009 | Weng et al. | 600/439 |
| 2010/0069797 A1 * | 3/2010 | Cain et al. | 601/2 |
| 2011/0028835 A1 | 2/2011 | Kawabata | |
| 2012/0010541 A1 * | 1/2012 | Cain et al. | 601/2 |

FOREIGN PATENT DOCUMENTS

| | | |
|---|---|---|
| JP | 2009-508649 | 3/2009 |
| WO | WO 98/01131 | 1/1998 |
| WO | WO 2007/038160 | 4/2007 |
| WO | WO 2007/038160 A2 | 4/2007 |
| WO | WO 2009/122650 | 10/2009 |
| WO | WO 2009/122650 A1 | 10/2009 |

OTHER PUBLICATIONS

Theresa M. Allen, Ligand-Targeted Therapeutics in Anticancer Therapy, Nature Reviews, Oct. 2002, pp. 750-763, vol. 2.

R. Glynn Holt, et al., Measurements of Bubble-Enhanced Heating From Focused, MHz-Frequency Ultrasound in a Tissue-Mimicking Material, Ultrasound in Med. Biol., Nov. 10, 2001, pp. 1399-1412, vol. 27, No. 10.

Christy K. Holland et al., Thresholds for transient cavitation produced by pulsed ultrasound in a controlled nuclei environment, J. Acoustical Society of America, Nov. 1990, pp. 2059-2069, vol. 88, No. 5.

Ken-ichi Kawabata, et al., Preliminary Study on Phase Shift Collides with Multiple Volatile Liquids for Site-Specific Contrast Imaging, 6th US Contrast.

\* cited by examiner

BEFORE EXPOSURE

1cm

AFTER PHASE-CHANGE
ULTRASOUND EXPOSURE

1cm

AFTER CAVITATIONAL ULTRASOUND
EXPOSURE(5 sec)

1cm

AFTER CAVIATIONAL ULTRASOUND
EXPOSURE(15 sec)

1cm

PHASE CHANGE ULTRASOUND

MICROBUBBLE SUSTENTION ULTRASOUND

THERAPEUTIC ULTRASOUND

ULTRASOUND DIAGNOSTIC AND TREATMENT DEVICE

TECHNICAL FIELD

The present invention relates to an ultrasound apparatus for diagnosis and therapy, and more particularly to an ultrasound technique for diagnosis and therapy using a phase-change-type ultrasound contrast agent and ultrasound in combination with each other.

BACKGROUND ART

It has been a while since medical imaging modalities such as an X-ray CT (Computed Tomography), MRI (Magnetic Resonance Imaging), or ultrasound diagnostic apparatus became essential tools in a medical practice. The systems described above visualize a difference in CT value, a difference in a proton relaxation time, or a difference in an acoustic impedance, in a living body, in a form of an image, and they are called "structural imaging", since the difference in physical properties exclusively reflects a structure (form) of a subject such as a living body.

On the other hand, the system that forms an image of portions, which have structurally the same tissue, but are functionally different from each other, is called "functional imaging". In the functional imaging, the system that visualizes molecular biological information, i.e., the presence of biocomponent molecules, such as protein, amino acid, or nucleic acid, is often called "molecular imaging". In the molecular imaging, a "molecular probe" that is a substance having a structure with selectivity for biocomponent molecules is often used, and in this case, a structure that can be detected with any physical means is applied to the molecular probe, in order to visualize the distribution of the molecular probe in a living body. For example, Non-Patent Literature 1 describes an example of a molecular probe when a target is a tumor. Peptide or antibody is a main molecular probe. A PET (Positron Emission Topography) device and optical imaging device can be provided as the imaging device that is specific to the molecular imaging described above.

In addition to the device specific to the molecular imaging, a system that detects and diagnoses disease, in their earlier stages than ever before, based upon a modality used in the existing structural imaging, such as MRI or ultrasound, has been developed. Among them, the system using ultrasound has characteristics not shared by the other modalities, which characteristics include that 1) the system is excellent in real-time nature, 2) the system is compact, so that it has less restriction for the use in an operation room, and 3) it can be used for not only diagnosis but also as a therapeutic tool, whereby it has been expected as an integrated diagnostic and therapeutic tool that can be used in even a place other than a large hospital.

The ultrasound used as the therapeutic tool enables a low-invasive therapy, in principle, because of spatial selectivity due to the exposure of the focused ultrasound from a site apart from a patient. A thermal coagulation therapy that increases the temperature of the target region to a protein-denaturation temperature (about 65 degrees Celsius) or more in a short period such as several seconds or several tens of seconds has received a lot of attention in recent years. It is often called HIFU therapy, since it is the therapy using high intensity focused ultrasound (HIFU) of 1 kW/cm² or more. In the HIFU therapy, spatial selectivity of therapy is achieved by the convergence of ultrasound alone, and therefore, the HIFU therapy has a possibility that, if the region is misaligned due to a body motion, high intensity ultrasound of 1 kW/cm² or more is exposed to a region other than the region to be treated, which causes serious adverse effect.

Therefore, a therapeutic method has been demanded that also achieves the spatial selectivity by a factor other than the convergence of the ultrasound, in order to realize safe and secure therapy. In order to attain the selectivity by a factor other than the ultrasound, a use of medical agent has been studied, and in particular, a therapeutic method using bubbles such as microbubbles that are frequently employed as an ultrasound contrast agent has been highly expected. For example, it has been found that, as described in Non-Patent Literature 2, an apparent absorption coefficient at tissues exposed to ultrasound increases due to the presence of the microbubbles. As the citation involved with the HIFU therapy and microbubbles, there are Non-Patent Literatures 3 and 4, and Patent Literatures 1 and 2, in addition to the above-mentioned Literature.

CITATION LIST

Patent Literature

Patent Literature 1: WO 98/01131
Patent Literature 2: WO 09/122650

Non-Patent Literature

Non-Patent Literature 1: Allen (2002) Nature Rev. Cancer 2: 750-763
Non-Patent Literature 2: Holt et al., (2001) Ultrasound Med. Biol. 27:1399-1412
Non-Patent Literature 3: Holland et al., (1990) J. Acoust. Soc. Am. 88: 2059-2069
Non-Patent Literature 4: Kawabata et al., (2004) Proc. 4th Intern. Symp. Ultrasound Contrast 1 mg. 92

SUMMARY OF INVENTION

Technical Problem

If microbubbles can be localized only on the target region in the HIFU therapy using bubbles such as microbubbles described above, only the target region can selectively be heated by utilizing this phenomenon. However, since the microbubble has a large size, it can exist in only a blood vessel, and it is difficult to allow the microbubble to move from the blood vessel to be localized on a specific region in a tissue.

Another problem in the HIFU therapy is that it is not sure whether a focus set by an apparatus and an actual focus in a living body agree with each other till an irreversible effect is caused on the living body due to the temperature rise or the generation of bubbles after the start of the therapy with the ultrasound exposure. In order to solve this problem, a process has to be needed in which a focus is found by the exposure of ultrasound with non-destructive intensity area, such as diagnostic ultrasound, which causes only a reversible bioeffect. However, it is difficult to determine the focus by the exposure of the ultrasound with the non-destructive intensity area such as the diagnostic ultrasound, in a living body having high tissue heterogeneity.

In addition, since a region that can be exposed by one exposure of the ultrasound is very small such as several cubic millimeters in the HIFU therapy, many regions have to be exposed with the focus being shifted. Accordingly, in order to surely perform the therapy in a short period, a process capable of monitoring the exposure of the ultrasound in a necessary and sufficient time has to be needed. However, in the thermal coagulation that is the mechanism of the HIFU therapy, it is often the case that a change by which a determination can clearly be made does not appear on a diagnostic image just after the therapy. Therefore, a method of confirming that the temperature rise is sufficient for the thermal coagulation through the temperature measurement by use of MRI, and a method in which a necessary intensity and time are calculated beforehand in consideration of the attenuation of ultrasound in the living body from the measurement result under water, and a hard-coded value is used for the therapy, are used. The characteristic of the HIFU therapy, which characteristic is that the region to be exposed in one exposure of the ultrasound is very small such as several cubic millimeters, and that the focus has to be shifted, also leads to a drawback of longer therapeutic time compared to the other methods. The portion where the intensity of the ultrasound is high is almost limited to the focus region, but since the ultrasound is emitted from sound sources as beams (toward focus), bioeffects of ultrasound, which are milder than the effect on the focus, occurs even on the region near the focus. Since the ultrasound energy is finally converted into thermal energy, in particular, the temperature increases on the region other than the focus. The portion near the sound source always receives the ultrasound, even if the focus is shifted, which produces further temperature rise. Under the above-mentioned circumstance, the HIFU therapy generally takes a process of performing the exposure of the ultrasound on the next focus after the temperature of the tissue is returned to the original temperature after the exposure of the ultrasound with the focus being defined on one portion. It takes about 10 to 30 seconds, in general, for the tissue to have the original temperature, so that, if the focus has to be shifted 100 times, for example, it takes 1 extra hour in addition to the actual therapeutic time.

There is also an effect of an (acoustic) cavitation as the ultrasound bioeffect involved with bubbles such as microbubbles. The cavitation is originally a phenomenon in which a nucleus of bubble is generated and increases its size, and finally collapses. The situation that the microbubbles are present on the region to which the ultrasound is to be emitted corresponds to the step where the bubble grows during the cavitation process, and one step of generating the nucleus, which is necessary for the induction of the cavitation, can be skipped by the exposure of the ultrasound with this state. Accordingly, it has been known that, as described in Non-Patent Literature 3, for example, the acoustic intensity necessary for inducing the cavitation is decreased because of the presence of the microbubbles. It has also been known that, when the cavitation is induced, a high temperature of several thousand degree Celsius and a high voltage of several hundred atmospheres are generated on the last stage where the bubble increases its size and collapses, and the bioeffect is directly caused by these or indirectly caused by a chemical substance called a sonochemically active agent described in Patent Literature 1, for example, whereby a cell death and tissue destruction are caused.

On the other hand, it has been studied that a phase-change chemical agent (phase-change nanodroplet) that is a droplet having nanosize upon an administration to a living body, and causes a phase change due to the exposure of the ultrasound so as to produce microbubbles is used as a contrast agent and a sensitizer for therapy in the HIFU. The droplet with the nanosize can be transferred into a tissue of a tumor, and tissue selectivity can be realized by employing the above-mentioned molecular imaging in which the molecular probe is added. A contrast-enhanced ultrasonography with high tissue selectivity can be realized by using the phase-change contrast agent described above. Since the phase-change nanodroplet forms a microbubble after the phase change, it can be applied as the HIFU sensitizer as described above. Since the size is small upon the administration, in particular, it is expected that the phase-change nanodroplet is distributed in a wider range than the range in the case of directly administering the microbubble, and is leaked out of the blood vessel to reach the tumor tissue, in particular.

As described above, the HIFU therapy can treat a tumor in a spatial-selective manner with low invasiveness, in principle. However, the HIFU therapy has problems that it takes long time for the therapy, that the focus for the therapeutic ultrasound cannot be determined by the ultrasound that does not produce the irreversible bioeffect, and that there is no way to check whether the necessary and sufficient ultrasound is transmitted or not during the exposure of the therapeutic ultrasound. Therefore, the HIFU therapy is in a situation of not exhibiting the fundamental superiority. The increase in the therapeutic time is caused from the situation that, since the HIFU therapy needs a high acoustic intensity, the degree of convergence is expected to be increased, and as a result, the focus region has to become smaller, in other words, it is a restriction of principle, and hence, it is unavoidable. Accordingly, it has been impossible to apply the HIFU therapy to a deep region where the temperature rise on the region other than the focus is likely to become a problem, and to a large tumor.

The present invention is accomplished in view of the above-mentioned circumstance, and aims to provide an ultrasound apparatus for diagnosis and therapy that can safely and surely make a diagnosis and therapy by use of a phase-change-type ultrasound contrast agent, while decreasing a therapeutic time for a subject, which is a target to be treated, more than ever before, whereby it can make a diagnosis and treatment for a depth region and a large tumor.

Solution to Problem

In order to attain the foregoing object, the present invention provides an ultrasound apparatus for diagnosis and therapy that emits ultrasound to a predetermined region of a target to be exposed for performing an ultrasound diagnosis and therapy, the apparatus including: a phase-change ultrasound transmit unit that emits phase-change ultrasound to the predetermined region to which an ultrasound contrast agent, which causes a phase change due to an exposure of ultrasound to become bubble, is administered; an ultrasound transmit unit for bubble sustention that emits ultrasound for bubble sustention for sustaining the generated bubble to the predetermined region; a therapeutic ultrasound transmit unit that emits therapeutic ultrasound to the predetermined region; and a control unit that controls the exposure of the ultrasounds from the phase-change ultrasound transmit unit, the ultrasound transmit unit for bubble sustention, and the therapeutic ultrasound transmit unit, wherein the control unit detects a bubble echo signal from the predetermined region, and can make control such that the therapeutic ultrasound is emitted to the predetermined region in a state in which the bubble is generated and sustained on the predetermined region.

In addition, in order to attain the foregoing object, the present invention provides an ultrasound apparatus for diagnosis and therapy that emits ultrasound to a therapy region of a target to be exposed for performing an ultrasound diagnosis and treatment, the apparatus including: a phase-change ultrasound transmit unit that emits phase-change ultrasound to the therapy region to which an ultrasound contrast agent, which causes a phase change due to an exposure of ultrasound to become bubble, is administered; an ultrasound transmit unit for bubble sustention that emits ultrasound for bubble sustention for sustaining the generated bubble to the therapy region; a therapeutic ultrasound transmit unit that emits therapeutic ultrasound to the therapy region; and a control unit that controls the exposure of the phase-change ultrasound, the ultrasound for bubble sustention, and the therapeutic ultrasound, acquires a bubble echo signal from the therapy region, and determines that the bubble is sustained on the therapy region when the intensity of the bubble echo signal is larger than a predetermined value.

Specifically, in order to attain the foregoing object, the present inventors have studied a high-speed ultrasound therapeutic method in combination with the phase-change nanodroplet, and a therapeutic apparatus for realizing this therapeutic method, and as a result, they have newly discovered that the short-lived bubbles, such as microbubbles, generated from the phase-change nanodroplet do not disappear but can exist by the exposure of the low intensity ultrasound with 0.72 W/cm$^2$ or less, that the low intensity ultrasound is not necessarily emitted continuously, and that the microbubbles sustained by the low intensity ultrasound become a nucleus of the acoustic cavitation by the exposure of the therapeutic ultrasound, and induces the acoustic cavitation effective for the treatment of a tumor.

Based upon the discoveries described above, in order to solve the problems described above, the site to be treated is set beforehand, the phase-change nanodroplet is administered, and the phase-change ultrasound and the ultrasound for microbubble sustention are emitted, while confirming the site with an image diagnosis, whereby the microbubbles caused by the phase-change nanodroplet are generated on the entire site to be treated, and the generated microbubbles are sustained. It has been found that the ultrasound technique for diagnosis and therapy in which, after it is confirmed from the image that the microbubbles are generated and sustained on all of the necessary places, and the therapeutic ultrasound is emitted to the entire site to be treated, is effective, and the present invention has been accomplished.

Specifically, in a preferable aspect of the ultrasound apparatus for diagnosis and therapy according to the present invention, the apparatus includes a therapeutic ultrasound generation unit that generates phase-change ultrasound for generating microbubbles from phase-change nanodroplet, ultrasound for microbubble sustention, which prevents the microbubbles generated by the phase change from disappearing, and therapeutic ultrasound for treating an entire site on which the sustained microbubbles are present; and an ultrasound diagnostic unit including a mechanism that visualizes a predetermined site to be treated with medical imaging and a positioning mechanism that can generate the microbubbles on the entire site to be treated displayed as the image, and a mechanism for detecting the microbubbles generated from the phase-change nanodroplet. In the ultrasound generation unit, the three types of ultrasounds, which are the phase-change ultrasound, the ultrasound for microbubble sustention, and the therapeutic ultrasound, can be emitted from the same sound source, or can be emitted from different sound sources respectively.

The feature of the present invention will be more apparent from the modes for carrying out the present invention described below and the attached drawings.

Advantageous Effect of Invention

According to the present invention, a treatment using focused ultrasound can surely be performed in a short period, and from this effect, the present invention can provide a technique of safely diagnosing and treating a subject.

DESCRIPTION OF EMBODIMENTS

The present invention relates to an ultrasound apparatus for diagnosis and therapy that generates microbubbles caused by a phase-change chemical agent on a target region due to an exposure of phase-change ultrasound under an administration of the phase-change chemical agent (phase-change nanodroplet), applies ultrasound for microbubble sustention in order to sustain the microbubbles generated by the exposure of the phase-change ultrasound for preventing the disappearance of the microbubbles, and applies therapeutic ultrasound to the entire target region to cause a heating action or a cavitation effect.

Various embodiments according to the present invention will be described below with reference to the attached drawings. In the embodiments of the ultrasound apparatus for diagnosis and therapy, a living body of an animal will be illustrated as a subject exposed to ultrasound. It is to be noted that the embodiments described below are only illustrative of realizing the present invention, and they do not limit the technical scope of the present invention. The common components in the figures are identified by the same numerals.

First Embodiment

A configuration and an operation of a first ultrasound apparatus for diagnosis and therapy will be described based upon FIGS. 1 to 5, 12, and 13.

<Configuration of Ultrasound Apparatus for Diagnosis and Therapy>

Figure 1:
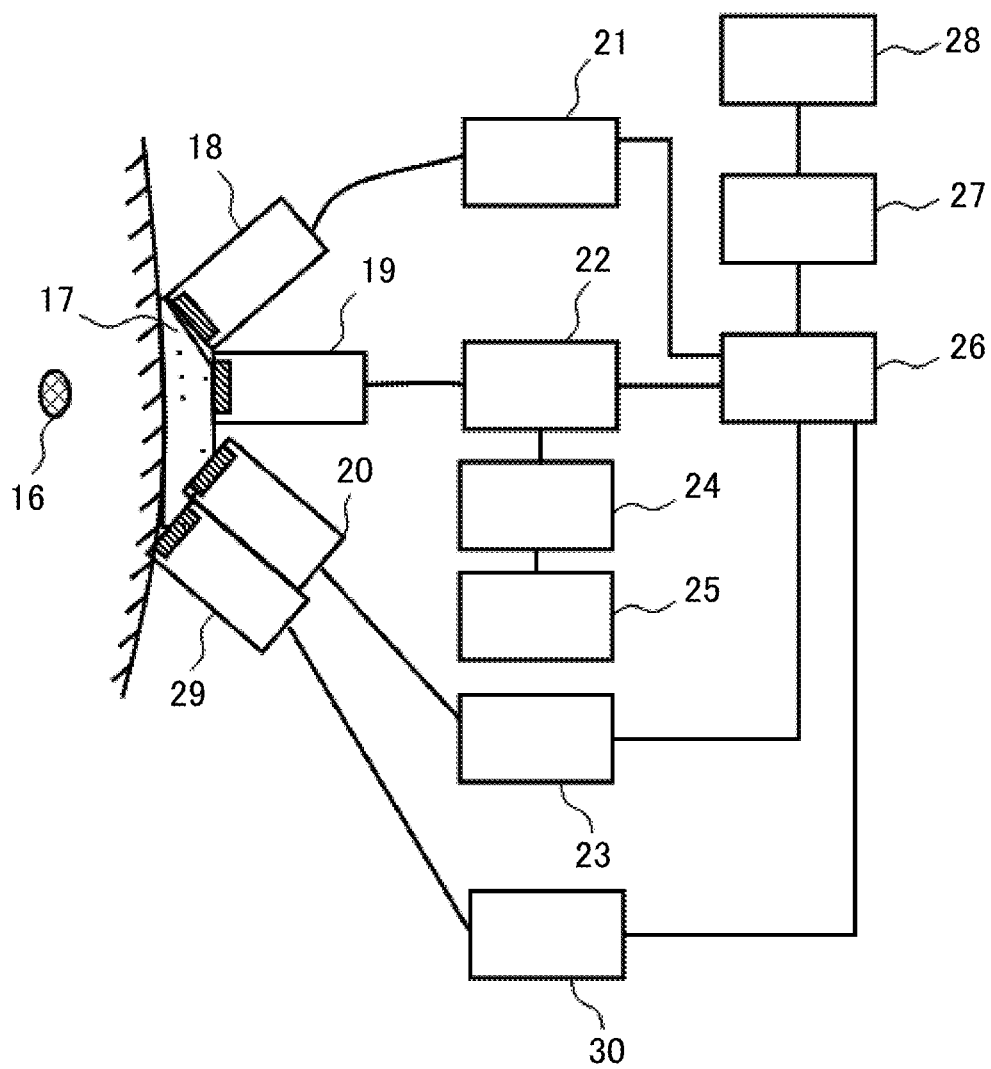
FIG. 1 is a view illustrating a schematic configuration of an ultrasound apparatus for diagnosis and therapy according to a first embodiment of the present invention.

FIG. 1 is a view illustrating one example of a schematic configuration of an ultrasound apparatus for diagnosis and therapy according to the first embodiment. In this figure, the ultrasound apparatus for diagnosis and therapy includes a phase-change ultrasound transmit unit 18 that is arranged for a therapy target (region) 16 through an acoustic coupling media 17 for exposing phase-change ultrasound, an ultrasound transmit unit 29 for microbubble sustention, which generates ultrasound for sustaining the microbubbles generated by a phase change, an ultrasound receive section for phase change unit 19 that emits phase-change detection ultrasound to the therapy target 16, and receives the phase-change detection ultrasound reflected from the therapy target 16, and a therapeutic ultrasound transmit unit 20 for emitting therapeutic ultrasound to the therapy target 16.

The ultrasound apparatus for diagnosis and therapy also includes a phase change ultrasound control unit 21 for controlling the exposure of the phase-change ultrasound, a phase-change detection ultrasound control unit 22 for controlling the exposure of the phase-change detection ultrasound, a control unit for microbubble sustention 30 for controlling the exposure of the ultrasound for microbubble sustention, and a therapeutic ultrasound control unit 23 for controlling the exposure of the therapeutic ultrasound, these control units being connected to the various ultrasound transmit units respectively.

The ultrasound apparatus for diagnosis and therapy also includes a signal processing unit for quantification of phase change 24 for quantifying the change caused by the phase change, a signal processing unit for therapy monitor 25 for monitoring the therapy, a central control unit 26 that executes the control of the whole apparatus, an image processing unit 27 that executes a predetermined image process needed for displaying the therapeutic process on a display unit, and an input and display unit 28 serving as an input and output unit for inputting information and outputting (displaying) information, these units being connected to the ultrasound control units. In the specification of this application, the ultrasound control units 21, 22, 23, and 30 and the central control unit 26 may collectively be referred to as a control unit. In any case, the central control unit 26 and the image processing unit 27 can be realized by a memory that is a memory unit of a general computer, and a programming process by a central processing unit (CPU) serving as a processing unit. The same applies to the signal processing unit for quantification of phase change 24 and the signal processing unit for therapy monitor 25, and they can be realized as a programming process of a single CPU.

Next, the ultrasounds emitted to the target to be exposed from the ultrasound transmit units in the present embodiment will be described. The phase-change ultrasound transmit unit 18 is configured to be capable of emitting i) ultrasound with a single frequency selected from a range of 0.5 to 2.5 MHz, or ii) ultrasound with a frequency that is selected from the range of 0.5 to 1.25 MHz and that becomes a reference, and with a frequency twice the reference frequency and with an acoustic intensity of 5 kW/cm$^2$ or less, considering energy loss in tissue. The ultrasound transmit unit 29 for microbubble sustention is configured to be capable of emitting ultrasound with a frequency of about 0.5 to 2.0 MHz and with a temporal mean intensity of 0.72 kW/cm$^2$ or less. The ultrasound receive section for phase change unit 19 is configured to be capable of transmitting ultrasound with a frequency of about 2 to 10 MHz and with a temporal mean intensity of 0.72 W/cm$^2$ or less, which ultrasound can be used in a general ultrasound diagnostic apparatus, and of receiving the ultrasound reflected from the therapy target 16.

On the other hand, the therapeutic ultrasound transmit unit 20 is configured to be capable of emitting i) ultrasound with a single frequency selected from the range of 0.5 to 2.5 MHz, or ii) ultrasound with a frequency that is selected from the range of 0.5 to 1.25 MHz, and that becomes a reference, and ultrasound with a frequency twice the reference frequency, in order to make a treatment by the heating action or the cavitation effect of the ultrasound. The acoustic intensity thereof can assume any value selected from the range of 50 to 1 kW/cm$^2$.

The phase-change ultrasound transmit unit 18 and the ultrasound transmit unit 29 for microbubble sustention are controlled such that 1) the ultrasound receive section for phase change unit 19 detects the phase change of the phase-change-type ultrasound contrast agent on the therapy region 16, the phase change being caused by the exposure of the ultrasound from the phase-change ultrasound transmit unit 18, and after the signal processing unit for quantification of phase change 24 confirms that the contrast agent is present on the therapy region through the image process, the exposure of the ultrasound from the ultrasound transmit unit 29 for microbubble sustention can be done, or 2) the phase-change ultrasound transmit unit 18 and the ultrasound transmit unit 29 for microbubble sustention synchronously start the exposure.

The signal processing unit for quantification of phase change 24 is configured to be capable of performing the image process for quantifying the change, such as the intensity or frequency component of the ultrasound echo signal (the signal including the phase-change detection ultrasound), caused by the phase change of the contrast agent, on receipt of the reception signal from the phase-change detection ultrasound control unit 22. In order to execute the quantification described above, the apparatus may include a recording unit of recording a signal before the phase change for holding the ultrasound echo signal before the exposure of the phase-change ultrasound, a recording unit of recording a signal after the phase change for holding the ultrasound echo signal during or after the exposure of the phase-change ultrasound, and a calculation unit that obtains a difference in a specific frequency component between the signals held in the respective recording units. It is needless to say that the recording units and the calculation unit can be realized by the memory and the programming process by the CPU as described above.

When the difference in the specific frequency component is obtained, it is desirable that even harmonic components of the central frequency of the phase-change ultrasound before and during the exposure of the phase-change ultrasound or after the exposure are compared. In order to detect the phase change during the exposure of the ultrasound for microbubble sustention from the ultrasound transmit unit 29 for microbubble sustention, in particular, the amplitude modulation of the ultrasound for microbubble sustention is executed by the control unit for microbubble sustention 30, and the magnitude of the modulated frequency component synchronized with this modulation is detected, whereby the detected signal can be defined as a phase-change signal.

The signal processing unit for therapy monitor 25 records the signal from the ultrasound receive section for phase change unit 19 during the exposure of the therapeutic ultrasound from the therapeutic ultrasound transmit unit 20, and records a temporal decrease in a signal on a region where the phase change occurs, and an increase in a signal of a peripheral region of the region where the phase change occurs.

<Content of Process of Ultrasound Apparatus for Diagnosis and Therapy>

The ultrasound apparatus for diagnosis and therapy according to the present embodiment can confirm a therapy region, while keeping the exposure time of the ultrasound to a minimum, and can make a treatment. For example, the apparatus can execute the process according to the operation flows illustrated in FIGS. 2 to 5.

1) Process when User Sets Therapy Target (Region)

Figure 2:
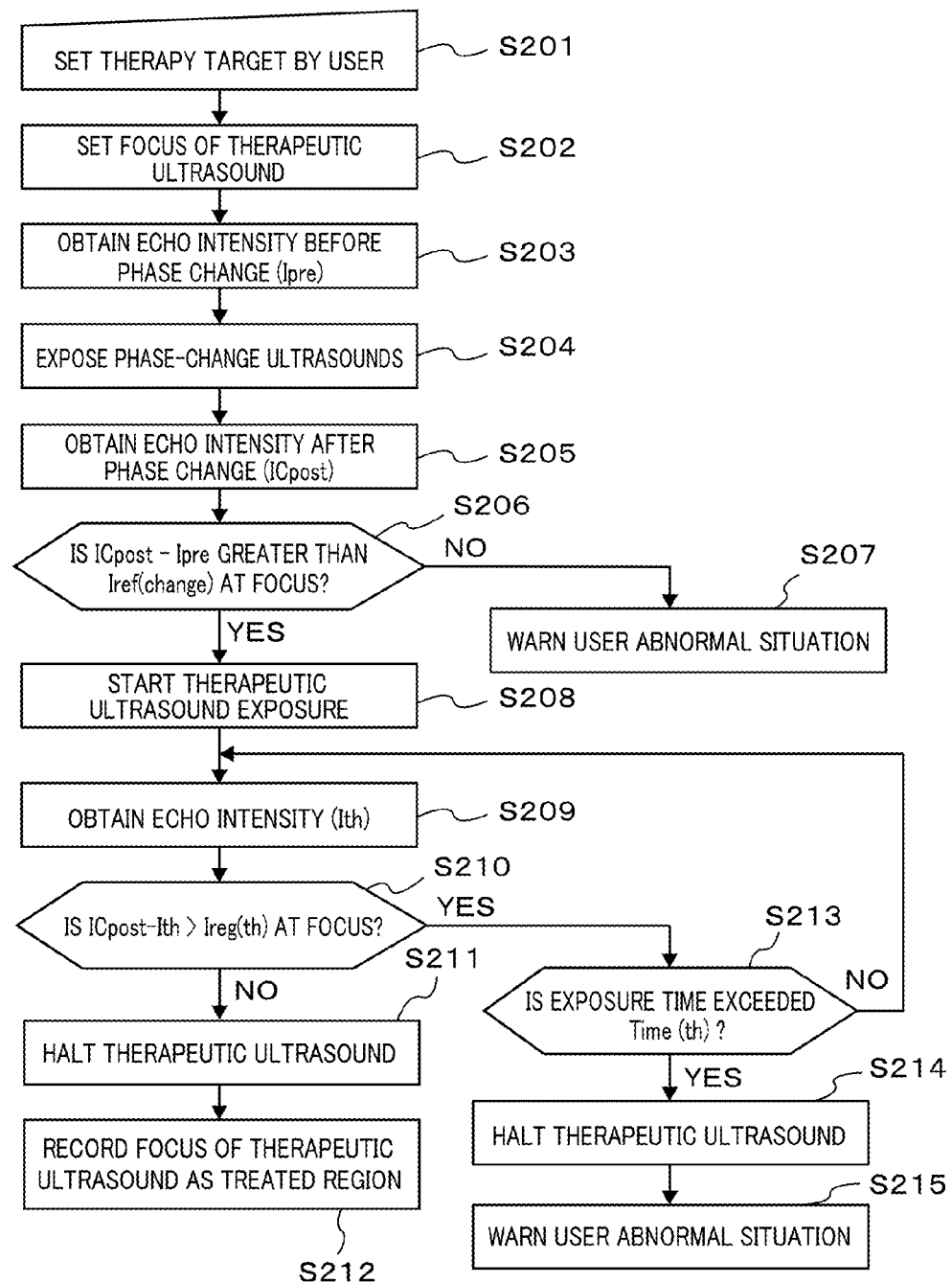
FIG. 2 is a view illustrating a flowchart of describing a process when a user sets a therapy target (region) in the ultrasound apparatus for diagnosis and therapy according to the first embodiment.

FIG. 2 is a flowchart for describing the content of the process when a user independently designates a focus by use of the input and display unit 28 for the therapy, because of the reason that the therapy target is small, and the like. The program corresponding to this flowchart is stored in the above-mentioned memory, and executed by the CPU. The same applies to the flowcharts described below.

Firstly, the input and display unit 28 accepts the therapy target set by the user on the screen of the apparatus (step S201). The central control unit 26 sets the region on which the phase change is to be generated by the phase-change ultrasound transmit unit 18, and the acoustic condition such as the intensity and length of the ultrasound for the phase change based upon a parameter preliminarily registered or a parameter inputted by the user (step S202).

Next, the central control unit 26 controls the ultrasound receive section for phase change unit 19 through the phase-change detection ultrasound control unit 22 so as to emit the phase-change detection ultrasound to the therapy target, to acquire an echo intensity Ipre before the phase change based upon the echo signal, and to store the resultant in the memory, not illustrated, in the apparatus for allowing the signal processing unit for quantification of phase change 22 to process the resultant (step S203). The central control unit 26 also controls the phase-change ultrasound transmit unit 18 through the phase change ultrasound control unit 21 based upon the setting described above so as to emit the phase-change ultrasound to the therapy target (step S204), and to acquire an echo intensity ICpost after the phase change by using the ultrasound receive section for phase change unit 19 (step S205).

Then, the central control unit 26 determines whether or not the value of "ICpost−Ipre" on the therapy target that is the therapy region is larger than a phase-change threshold value Iref(change) that is a predetermined value (step S206). When the value of "ICpost−Ipre" is smaller than the Iref(change), the central control unit 26 warns the user of an abnormal situation, since this situation means that the phase change is not generated, and hence, the central control unit 26 suspends the therapy (step S207).

When the value of "ICpost−Ipre" is larger than the Iref (change), the central control unit 26 controls the therapeutic ultrasound transmit unit 20 through the therapeutic ultrasound control unit 23 so as to start the exposure of the ultrasound, having the intensity and pulse length preliminarily registered or set by the user, to the therapy target 16 (step S208). The ultrasound receive section for phase change unit 19 acquires the intensity Ith of the echo signal at the focus, i.e., on the region where the phase change is generated, at a time interval set beforehand (step S209). The central control unit 26 determines whether or not the value (ICpost−Ith) obtained by subtracting the intensity Ith of the echo signal from the echo intensity (ICpost) just after the exposure of the phase-change ultrasound is larger than the threshold value (ratio) Iref(th) preliminarily registered or set by the user (step S210).

In the case of (ICpost−Ith<Iref(th)), the central control unit 26 controls the therapeutic ultrasound transmit unit 20 through the therapeutic ultrasound control unit 23 so as to stop the exposure of the therapeutic ultrasound (step S211). Then, the central control unit 26 records the focus as the treated region where the treatment has already been completed, and displays this region as being distinguished from the other region on the screen (step S212).

In the case of (Ipost−Ith>Iref(th)), the central control unit 26 stops the exposure of the ultrasound through the control of the therapeutic ultrasound transmit unit 20 via the therapeutic ultrasound control unit 23, when the exposure time of the therapeutic ultrasound is longer than the maximum treatment time Time(th) preliminarily registered or set by the user (Yes in step S213→S214), records that the treatment is incomplete, and warns the user of this situation (step S215). When the exposure time of the therapeutic ultrasound is shorter than the maximum treatment time Time(th) preliminarily registered or set by the user (No in step S213), the process proceeds to step S209.

Figure 3:
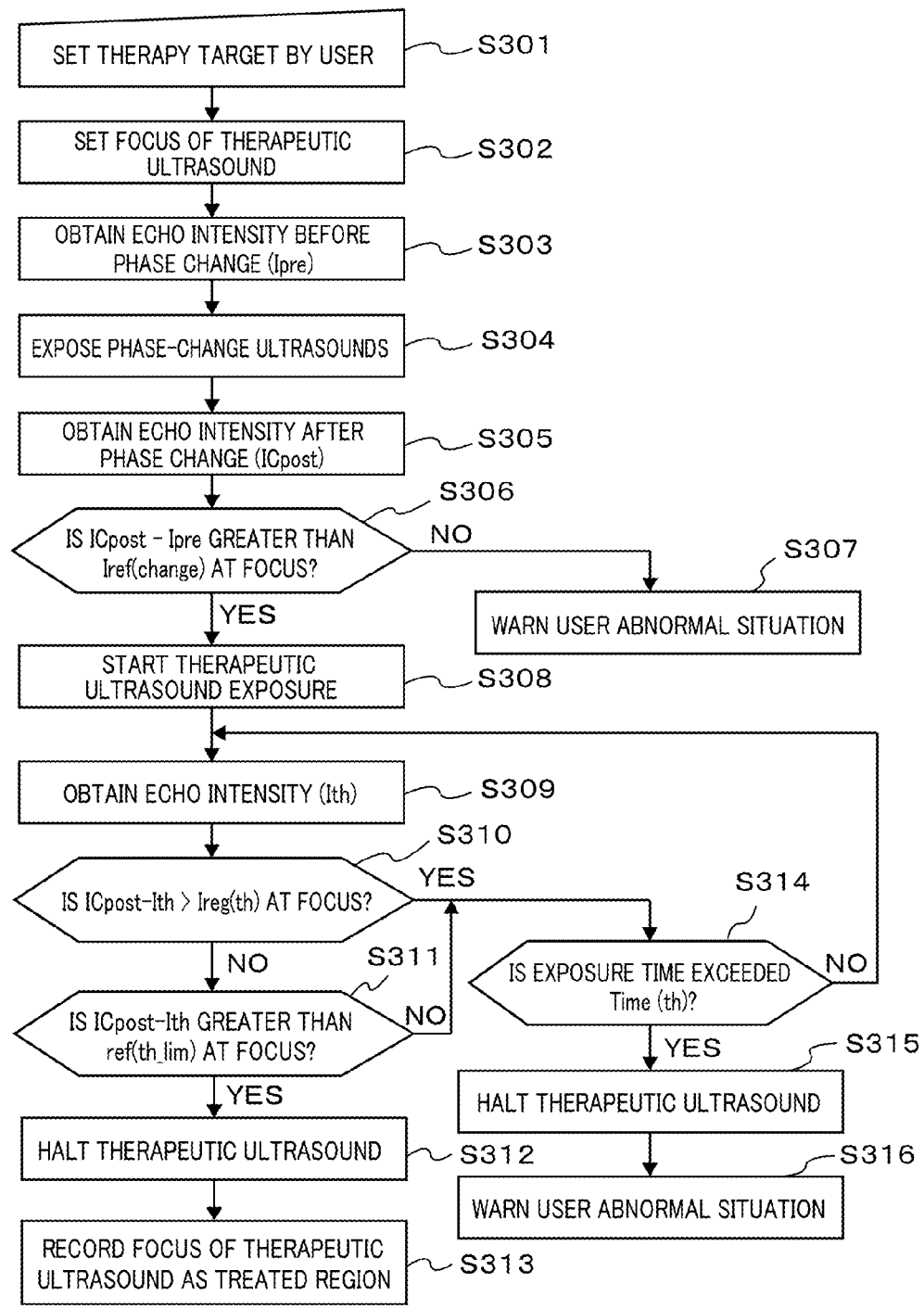
FIG. 3 is a flowchart for describing a process in which a user sets a therapy target (region), and exactly determines a completion of a therapy in the ultrasound apparatus for diagnosis and therapy according to the first embodiment.

2) Process in Case where User Sets Therapy Target, and in Case where User Needs to Exactly Know Completion of Therapy, in Particular FIG. 3 is a flowchart illustrating the process in case where the user sets the therapy target, and in case where the user needs to exactly know the completion of the therapy, in particular. The program corresponding to this flowchart is also stored in the memory, not illustrated in FIG. 1, and is executed by the CPU serving as a processing unit.

The process illustrated in FIG. 3 is basically the same as the process illustrated in FIG. 2, but as the condition of the completion of the therapeutic ultrasound, a process (step S311) of determining which is larger, ICpost−Ith or a threshold value Iref(th_lim), set beforehand, in the vicinity of the therapy target is also performed in addition to the process (S310) of determining which is larger, the ICpost−Ith or Iref (th) on the focus. Specifically, in the case of ICpost−Ith<Iref (th) (No in step S310), and ICpost−Ith>Iref(th_lim) in the vicinity of the focus (Yes in step S311), the central control unit 26 controls the therapeutic ultrasound transmit unit 20 through the therapeutic ultrasound control unit 23 so as to normally end the exposure of the ultrasound (step S312), to record the focus region satisfying the conditions described above as the treated region where the therapy has already been completed, and to display this region as being distinguished from the other region on the screen (step S313).

Figure 4:
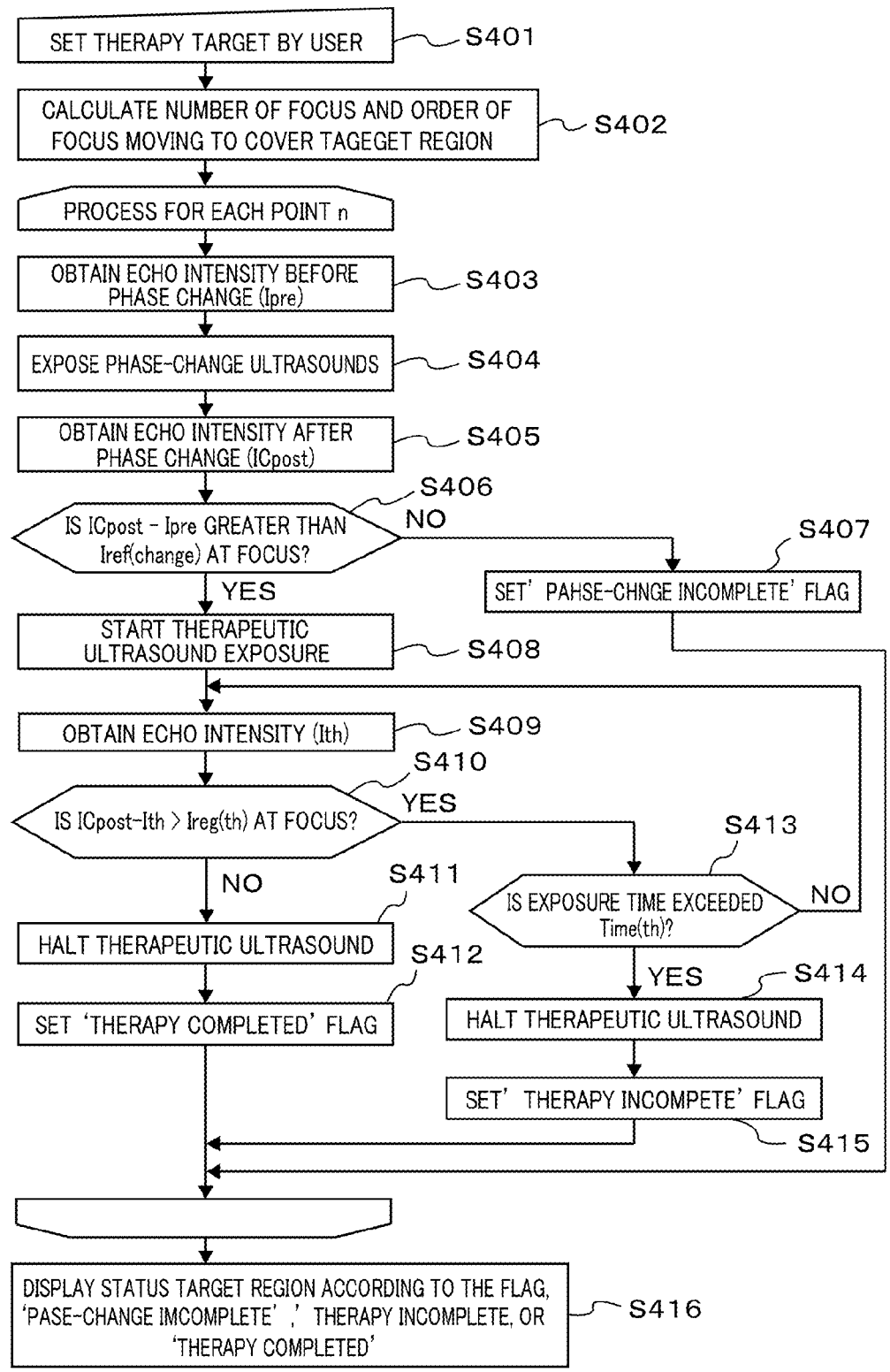
FIG. 4 is a view illustrating a flowchart of describing a process when a user sets a therapy range in the ultrasound apparatus for diagnosis and therapy according to the first embodiment.

3) Process in Case where User Sets Therapy Range, and Apparatus Calculates Number of Focuses and Order of Focus Moving FIG. 4 is a flowchart illustrating the process in case where the user sets a therapy range, and the apparatus calculates a number of focuses and order of focus moving. The program corresponding to this flowchart is also stored in the memory, not illustrated in FIG. 1, and is executed by the CPU serving as a processing unit.

The process illustrated in FIG. 4 is basically the same as the process illustrated in FIG. 2, but in FIG. 4, the user does not directly set the focus for therapy, but sets the therapy region and therapy range, the central control unit 26 sequentially sets the number of focuses and the order of focus moving, which are optimum for perfectly covering the target region, based upon the setting and the parameter preliminarily registered by the apparatus or set by the user, and the therapy is done for each focus. In the case where ICpost−Ipre is smaller than Iref(change), the central control unit 26 sets a phase-change flag (step S407); in the case where ICpost−Ith is larger than Iref(th) even if the therapeutic ultrasound is exposed for a period longer than Time(th), the central control unit 26 sets a therapy incomplete flag (step S415); and in the case where the therapy is normally completed, the central control unit 26 sets a therapy completed flag (step S412). The central control unit 26 displays in order that the user can clearly recognize where the therapy t is normally completed or not within the therapy range by using these flags (step S416).

Figure 5:
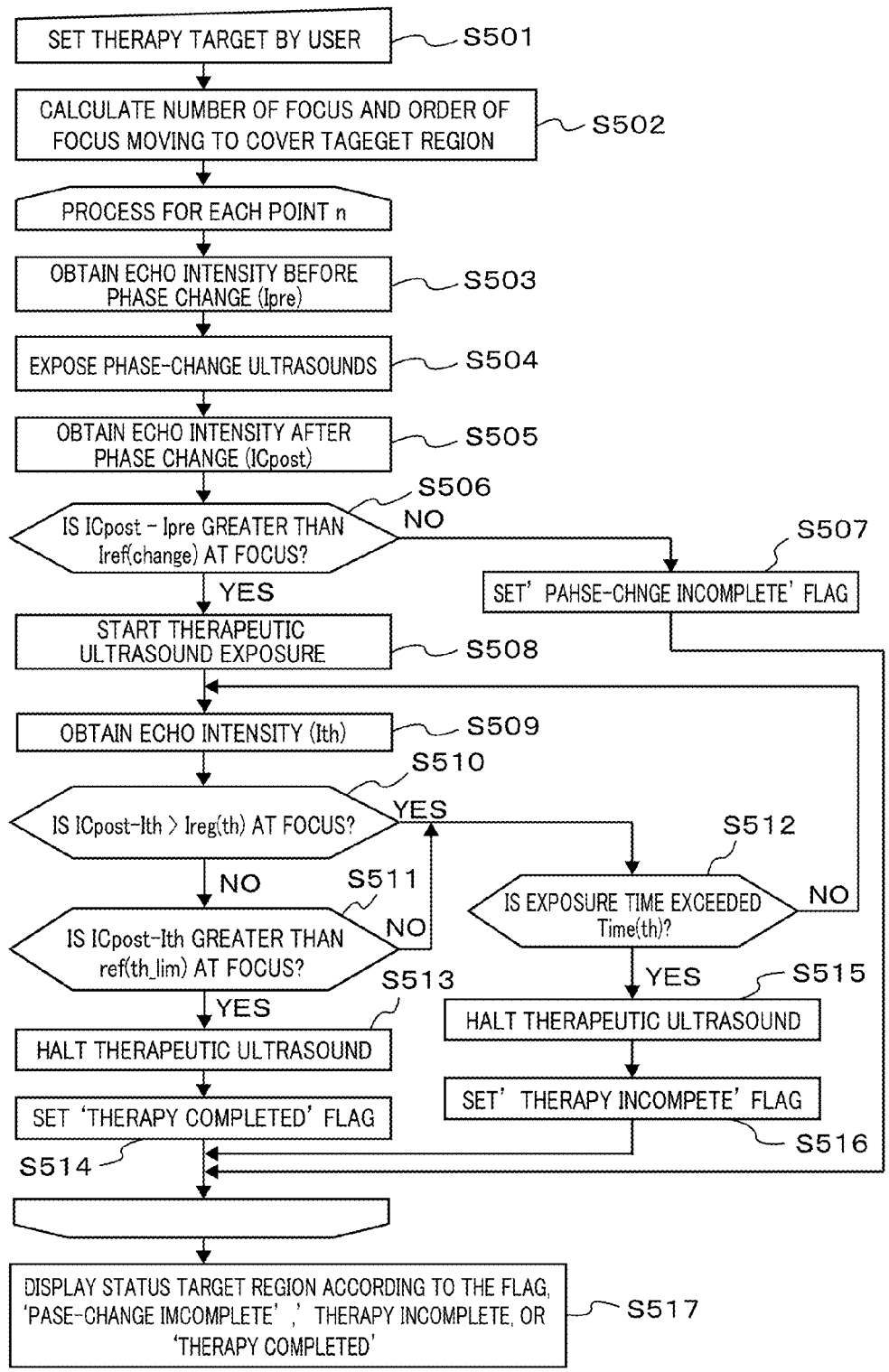
FIG. 5 is a flowchart for describing a process in which a user sets a therapy region, and exactly determines a completion of a therapy in the ultrasound apparatus for diagnosis and therapy according to the first embodiment.

4) Process in Case where User Sets Therapy Range, Apparatus Calculates Number of Focuses and Order of Focus Moving, and in Particular, User Needs to Exactly Know Completion of Therapy FIG. 5 is a flowchart illustrating the process in case where the user sets the therapy range, the apparatus calculates a number of focuses and order of focus moving, and in particular, the user needs to exactly know completion of the therapy. The program corresponding to this flowchart is also stored in the memory, not illustrated in FIG. 1, and is executed by the CPU serving as a processing unit.

The process illustrated in FIG. 5 is basically the same as the process illustrated in FIG. 4, but as the condition of the completion of the therapeutic ultrasound, a process (step S511) of determining which is larger, ICpost−Ith or a threshold value Iref(th_lim), set beforehand, in the vicinity of the therapy target is also performed in addition to the process (S510) of determining which is larger, the ICpost−Ith or Iref (th) on the focus. Specifically, in the case of ICpost−Ith<Iref (th) (No in step S510), and ICpost−Ith>Iref(th_lim) in the vicinity of the focus (Yes in step S511), the central control unit 26 controls the therapeutic ultrasound transmit unit 20 through the therapeutic ultrasound control unit 23 so as to normally end the exposure of the ultrasound (step S513).

<Example of Exposure Sequence of Phase-Change Ultrasound, Phase-Change Detection Ultrasound, and Microbubble Sustention Ultrasound>

Various process flows for a therapy, while confirming the therapy target and suppressing the exposure time of the ultrasound to the minimum necessary in the ultrasound apparatus for diagnosis and therapy according to the present embodiment have been described above. Subsequently, the exposure sequence of the phase-change ultrasound, the phase-change detection ultrasound, and the microbubble sustention ultrasound for efficiently performing the processes described above will be described with reference to FIGS. 12 and 13.

Figure 12:
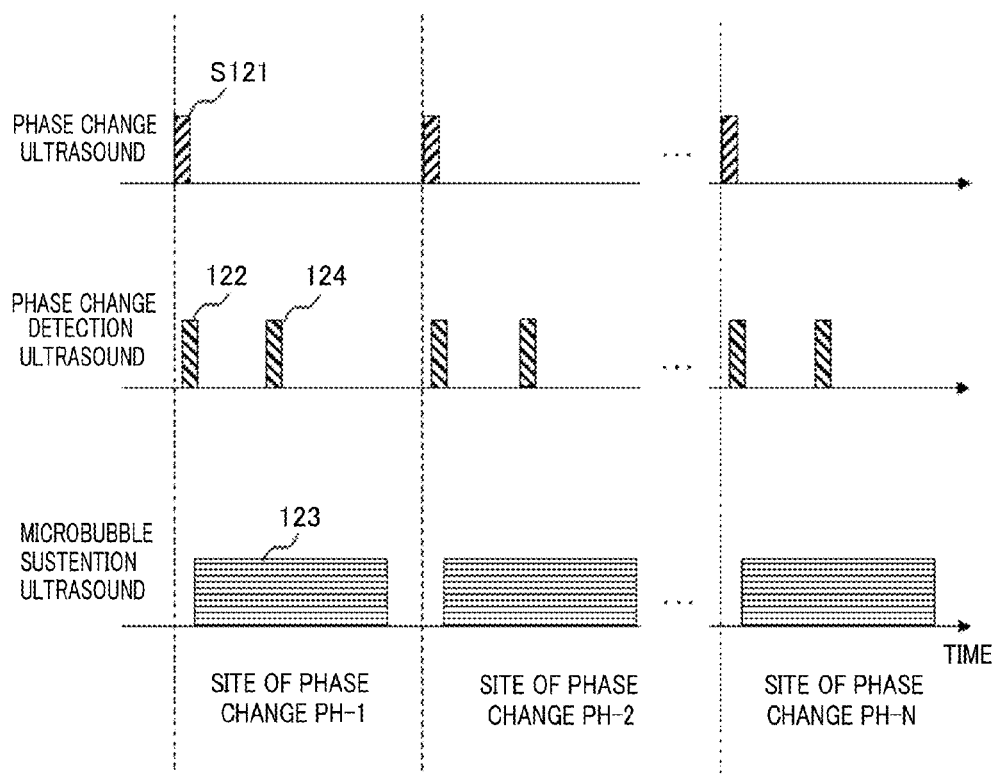
FIG. 12 is a view illustrating one example of an exposure sequence of ultrasound in the ultrasound apparatus for diagnosis and therapy according to the first embodiment.

Examples of the exposure sequence of the phase-change ultrasound, the phase-change detection ultrasound, and the microbubble sustention ultrasound are respectively illustrated in an upper chart, in a middle chart, and in a lower chart in FIG. 12, wherein an abscissa axis indicates time, and an ordinate axis indicates the intensity. As illustrated in FIG. 12, the phase-change ultrasound is sequentially transmitted to the sites of phase change PH-1, PH-2, . . . PH-N. These ultrasounds are respectively transmitted from the phase-change ultrasound transmit unit 18, the ultrasound receive section for phase change unit 19, and the ultrasound transmit unit 29 for microbubble sustention according to the controls of the corresponding control units 21, 22, and 30 in the ultrasound apparatus for diagnosis and therapy in FIG. 1.

In steps S201 and S202 in FIG. 2, the sites PH-1~PH-N, to which the phase-change ultrasound is to be emitted, in the therapy region are set. Firstly, phase-change ultrasound 121 is sequentially emitted to each of the sites PH-1 PH-N, and just after this, phase-change detection ultrasound 122 is emitted to confirm whether microbubbles are generated or not due to the phase change. When it is confirmed that the microbubbles are generated, microbubble sustention ultrasound 123 is emitted. After a period set beforehand, phase-change detection ultrasound 124 is again emitted to confirm that the microbubbles are sustained. Specifically, it is controlled such that, after the exposure of the phase-change ultrasound 121, the phase-change detection ultrasounds 122 and 124 are synchronously emitted. The microbubble sustention ultrasound 123 can be continuously emitted, or can be emitted in a form of a pulse as illustrated later by a specific example.

The above-mentioned sequence is continuously performed to PH-1 to PH-N. In this case, the phase-change ultrasound and the phase-change detection ultrasound are emitted on the focus in such a manner that the sites PH-1 to PH-N to be exposed are shifted. On the other hand, the microbubble sustention ultrasound is emitted to the sites PH-1 to PH-N, to which the treatment is to be done, with an intensity of 0.72 W/cm$^2$ or more at all times. After the phase change is generated on all of the sites PH-1 to PH-1, the therapeutic ultrasound not illustrated is emitted in order that the region including PH-1 to PH-N can be exposed to the ultrasound having sufficient intensity for the therapy for a time sufficient for the therapy. When the microbubble sustention ultrasound or the therapeutic ultrasound cannot cover the region from PH-1 to PH-N because the size of the tumor is large, the therapy region is divided, and then, the therapy is done.

Figure 13:
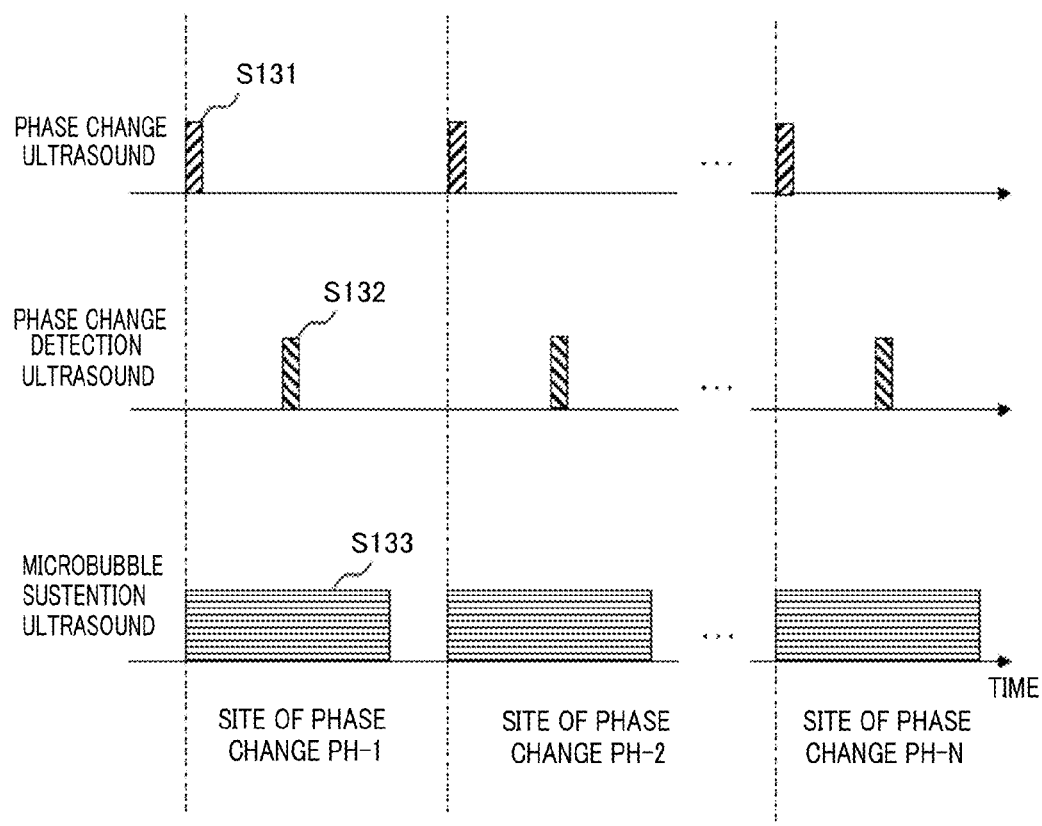
FIG. 13 is a view illustrating another example of the exposure sequence of ultrasound in the ultrasound apparatus for diagnosis and therapy according to the first embodiment.

An example of a different exposure sequence will be described with reference to FIG. 13. In this example, the sites PH-1 to PH-N in the therapy region which is exposed to phase-change ultrasound 131 are set in steps S201 and S202 in FIG. 2. The phase-change ultrasound 131 and microbubble sustention ultrasound 133 are simultaneously emitted to each of the sites PH-1 to PH-N one by one, and after a period set beforehand, phase-change detection ultrasound 132 is emitted. When it is confirmed that the microbubbles are generated, the next site then becomes the target. The sequence described above is continuously performed from PH-1 to PH-N. Specifically, the phase-change ultrasound transmit unit 18 and the ultrasound transmit unit 29 for microbubble sustention are controlled to synchronously start the exposure, and it is controlled such that the phase-change detection ultrasound 132 is emitted in synchronous with these ultrasounds.

In this case, the phase-change ultrasound 131 and the phase-change detection ultrasound 132 are emitted on the focus in such a manner that the sites PH-1 to PH-N to be exposed are shifted, and on the other hand, the microbubble sustention ultrasound 133 is emitted to the sites PH-1 to PH-N, to which the treatment is to be done, with an intensity of 0.72 W/cm² or more at all times, as in the exposure sequence in FIG. 12. After the phase change is generated on all of the sites PH-1 to PH-1, the therapeutic ultrasound not illustrated is emitted in order that the region including PH-1 to PH-N can be exposed to the ultrasound having sufficient intensity for the therapy for a time sufficient for the therapy. When the microbubble sustention ultrasound or the therapeutic ultrasound cannot cover the region from PH-1 to PH-N because the size of the tumor is large, the therapy region is divided, and then, the treatment is done, as in the exposure sequence in FIG. 12.

Second Embodiment

<Example of Providing Plural Functions to One Ultrasound Exposure Apparatus>

The ultrasound apparatus for therapy illustrated in FIG. 1 having the configuration described above transmits and receives four types of ultrasounds, which are the phase-change ultrasound, phase-change detection and confirmation ultrasound, microbubble sustention ultrasound, and therapeutic ultrasound. For the phase-change detection ultrasound, an ultrasound receive section having a function equivalent to the function of a probe for a normal ultrasound diagnostic device is exclusively used, but it is considered to be advantageous for simplifying the apparatus and securing safety by using the same ultrasound exposure apparatus for the other ultrasounds. A second embodiment in which a single ultrasound exposure apparatus has plural functions will be described below with reference to the drawings.

Figure 14A:
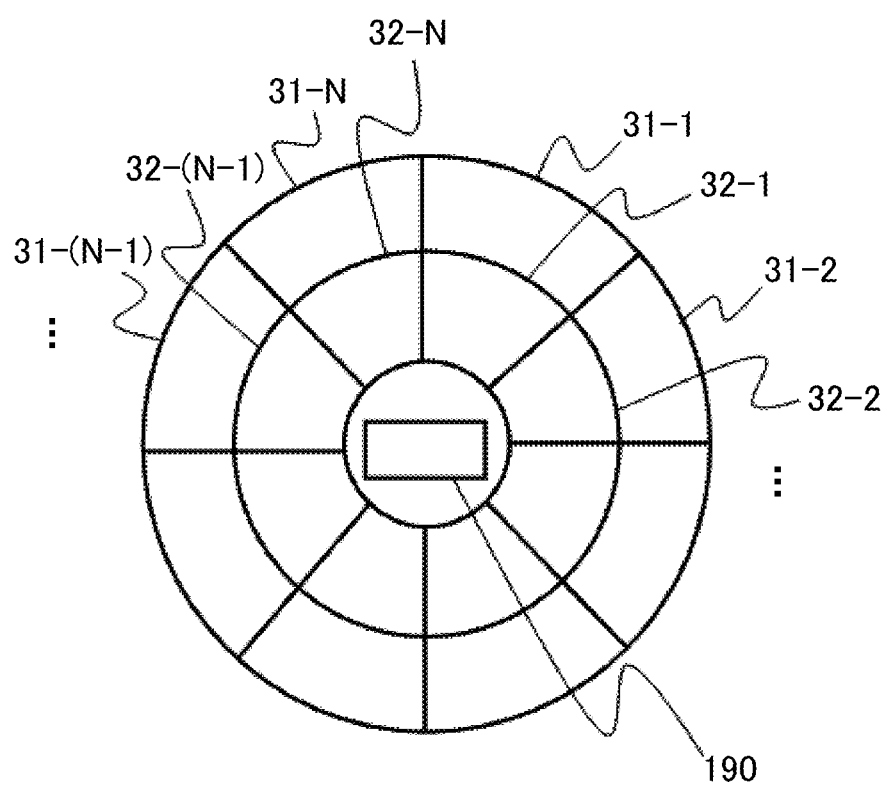
FIG. 14A is a plan view illustrating one example of a configuration of an ultrasound apparatus for diagnosis and therapy according to a second embodiment.
Figure 14B:
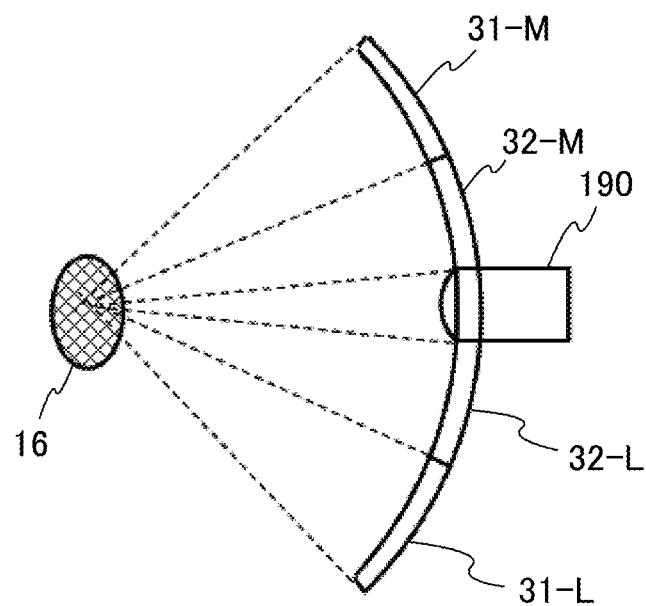
FIG. 14B is a sectional view illustrating one example of the configuration of the ultrasound apparatus for diagnosis and therapy according to the second embodiment.

FIGS. 14A and 14B are schematic views illustrating one example of a transducer, i.e., the ultrasound exposure apparatus, having the plural functions, wherein FIG. 14A is a plan view, and FIG. 14B is a sectional view at any angle passing through the center. An ultrasound exposure apparatus 190 according to the present invention has a concave bowl-like shape, and is provided with outer piezoelectric elements (hereinafter abbreviated to outer elements) 31-1 to 31-N, and inner piezoelectric elements (hereinafter abbreviated to inner elements) 32-1 to 32-N, wherein the outer piezoelectric elements and inner piezoelectric elements are doubly arranged. The outer piezoelectric elements 31-1 to 31-N and the inner piezoelectric elements 32-1 to 32-N are configured such that the amplitude and phase of each element can independently be controlled. In FIG. 14B, numerals 31-M, 31-L, 32-M, and 32-L indicate the outer and inner piezoelectric elements located on a cross-section at a predetermined angle. The outer and the inner are only conceptual in the present invention, and they may be a set of piezoelectric elements that are finely divided.

Figure 15A:
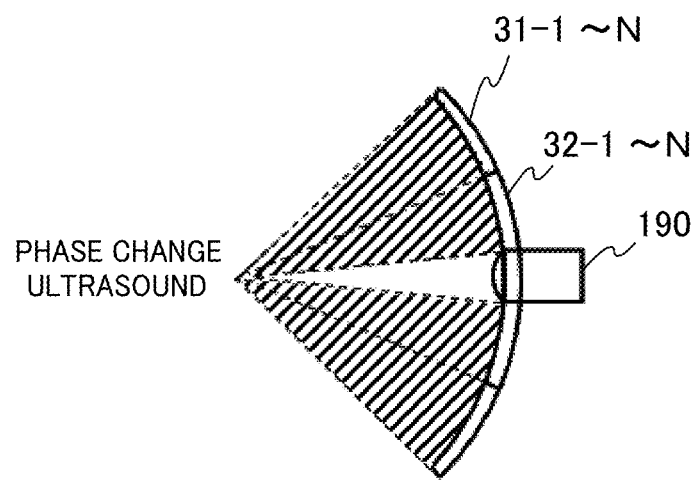
FIG. 15A is a view illustrating one example of a method of selecting ultrasound exposure source according to the second embodiment.
Figure 15B:
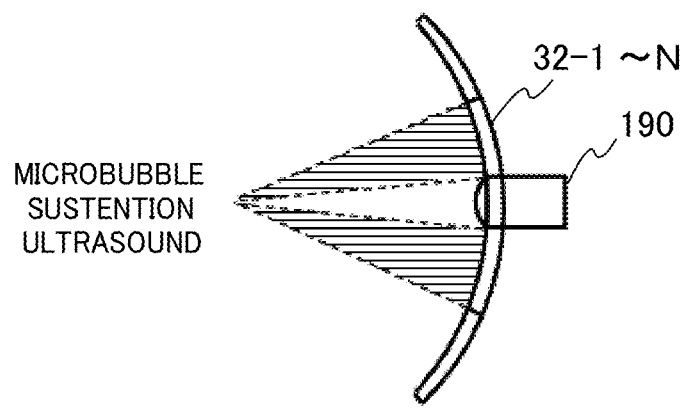
FIG. 15B is a view illustrating one example of a method of selecting ultrasound exposure source according to the second embodiment.
Figure 15C:
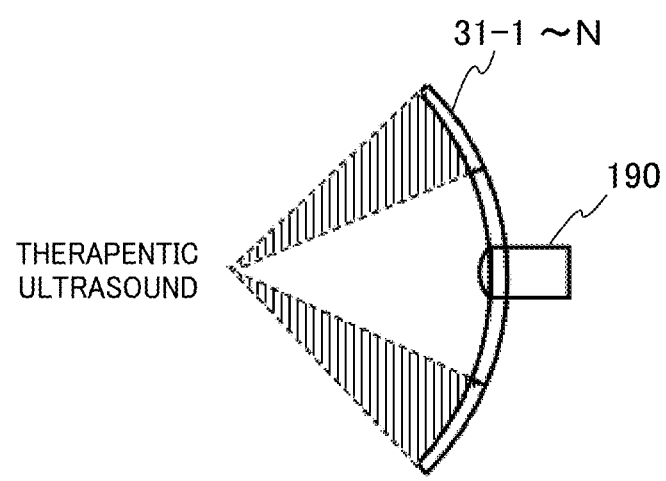
FIG. 15C is a view illustrating one example of a method of selecting ultrasound exposure source according to the second embodiment.

A method of selecting the ultrasound exposure source for the phase-change ultrasound, the phase-change detection ultrasound, the microbubble sustention ultrasound, and the therapeutic ultrasound by use of the ultrasound exposure apparatus 190 illustrated in FIGS. 14A and 14B will be described with reference to FIGS. 15A, 15B, and 15C. As previously described, the highest acoustic pressure is needed to emit the phase-change ultrasound, so that the ultrasound is emitted to be focused on the target site by using all of the outer piezoelectric elements 31-1 to 31-N and the inner piezoelectric elements 32-1 to 32-N as illustrated in FIG. 15A. When the microbubble sustention ultrasound is emitted, only the inner piezoelectric elements 32-1 to 32-N are used to increase the focus region. The size of the focus region can be controlled by using only some of the inner elements 32-1 to N depending upon the size of the therapy region 16, or by controlling the phase of the waveform applied to each of the inner piezoelectric elements 32-1 to N. As illustrated in FIG. 15C, when the therapeutic ultrasound is emitted, only the outer piezoelectric elements 31-1 to N are used to make it possible to generate the ultrasound intensity higher than the microbubble sustention ultrasound. The size of the focus region of the therapeutic ultrasound can be controlled by using only some of the outer elements 31-1 to N depending upon the size of the therapy region 16, or by controlling the phase of the waveform applied to each of the outer piezoelectric elements 31-1 to N.

Figure 16A:
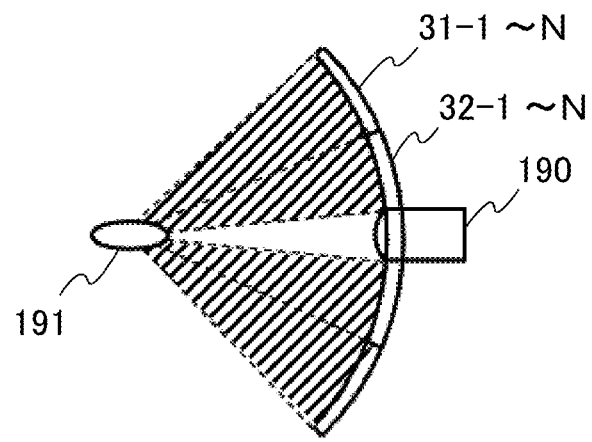
FIG. 16A is a view illustrating one example of a method of selecting ultrasound exposure source according to the second embodiment.
Figure 16B:
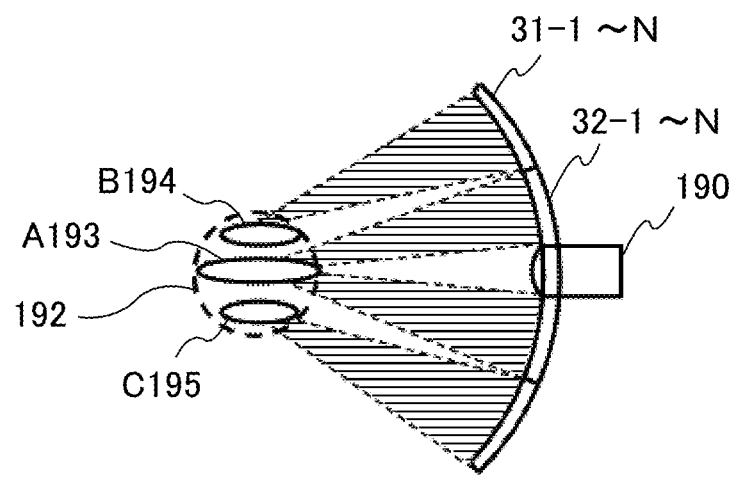
FIG. 16B is a view illustrating one example of a method of selecting ultrasound exposure source according to the second embodiment.
Figure 16C:
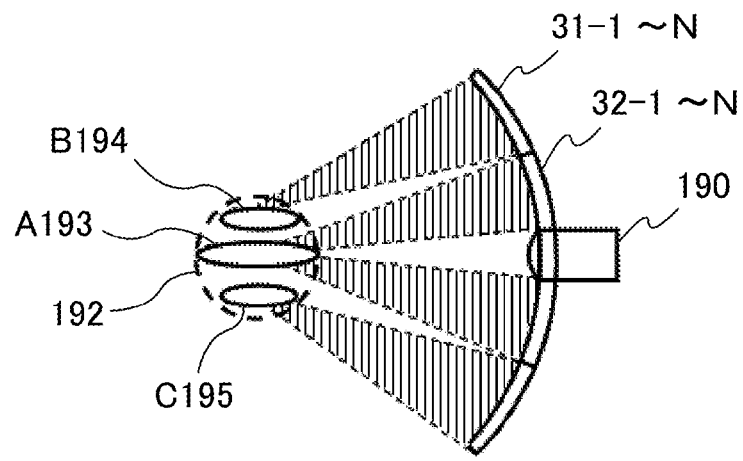
FIG. 16C is a view illustrating one example of a method of selecting ultrasound exposure source according to the second embodiment.

Subsequently, a different example of use of the ultrasound exposure apparatus according to the present embodiment will be described with reference to FIGS. 16A, 16B, and 16C. In this example, the phase-change ultrasound, the microbubble sustention ultrasound, and the therapeutic ultrasound are all emitted by using all of the outer piezoelectric elements 31-1 to 31-N and the inner piezoelectric elements 32-1 to 32-N. However, as illustrated in FIG. 16A, the phase-change ultrasound is emitted such that all elements are converged on a focus region 191, in the case of the exposure of the phase-change ultrasound. On the other hand, in the exposure of the microbubble sustention ultrasound and the therapeutic ultrasound, the ultrasound is emitted such that each of the outer elements 31-1 to 31-N is converged on a focus B194 or a focus C195, which are symmetrically different, and such that each of the inner elements 32-1 to 32-N is converged on a focus A193 that is symmetrically different from the focuses B194 and the 195C. According to the exposure described above by using a single ultrasound exposure apparatus in the present embodiment, a single virtual focus region 192 is formed, whereby the phase-change ultrasound that needs a high ultrasound intensity, and the microbubble sustention ultrasound and the therapeutic ultrasound, which require a wide focus region, can be used depending upon occasions.

EXPERIMENTS

Experiments based upon the above-mentioned embodiments will specifically be described below.

1) Experiment 1

Figure 6:
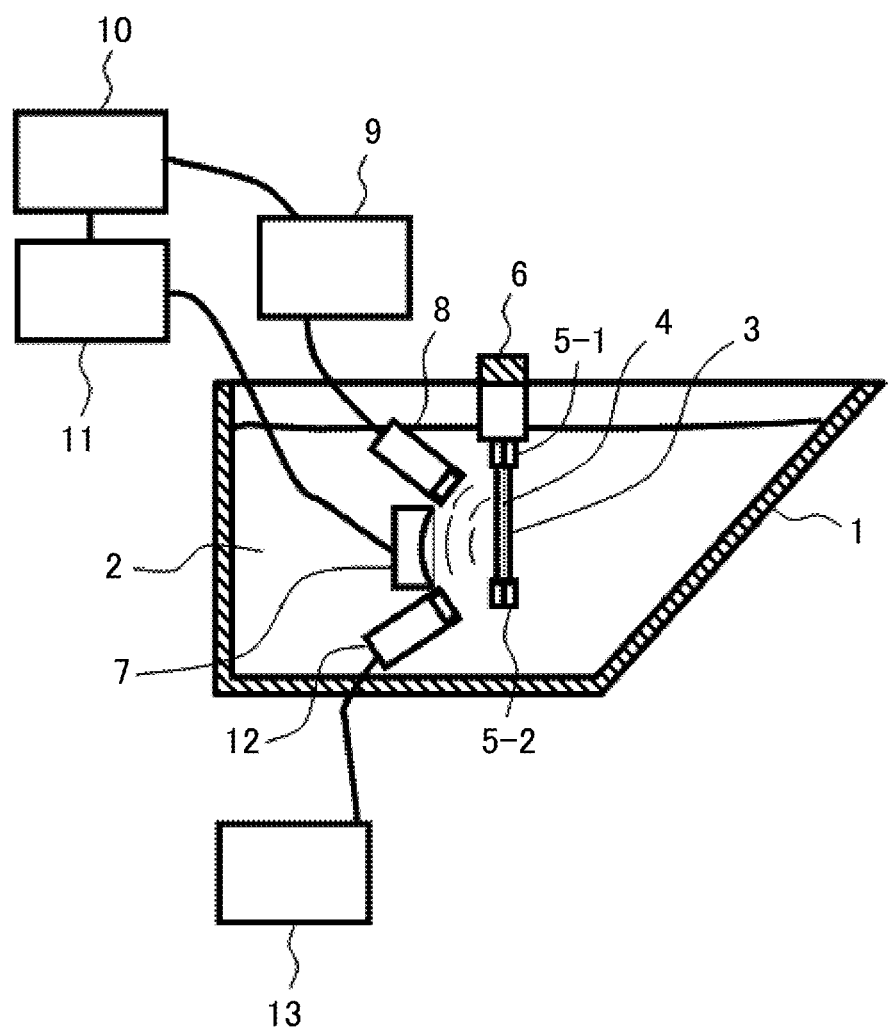
FIG. 6 is a view illustrating an example of a configuration of a device in an experimental system in an experiment 1 carried out for checking a relationship between an induction of a cavitation and an echo signal intensity by an exposure of ultrasound in water according to the first embodiment.

Relationship (in Water) Between Generation of Acoustic Cavitation and Change in Intensity of Echo Signal Due to Exposure of Ultrasound FIG. 6 illustrates an experimental system used for checking a relationship between how much the acoustic cavitation occurs in water and a change in an intensity of an echo signal observed in a medical ultrasound scanner. The system in FIG. 6 is different from the apparatus in FIG. 1 according to the embodiment 1, but a transducer 7 serving as an ultrasound exposure apparatus corresponds to a component formed by combining the ultrasound receive section for phase change unit 19 and the therapeutic ultrasound transmit unit 20, and an ultrasound diagnostic probe for phase change monitoring 8 corresponds to the phase-change ultrasound transmit unit 18. A component formed by combining a wave generator 10 for a phase-change waveform and an acoustic cavitation and an amplifier 11 corresponds to the component formed by combining the phase-change detection ultrasound control unit 22 and the therapeutic ultrasound control unit 23.

As illustrated in FIG. 6, a sample containing tube 3 containing a sample 4 is held in water by use of clips 5-1 and 5-2 for fixing edge of the tube, and a sample holder 6 in a state in which degassed water 2 maintained at 37 degree Celsius is filled in a plastic water tank 1. The focused ultrasound transducer 7 for the phase change of the sample and cavitation induction (for therapy) has a diameter 40 mm, and f-number of 1, and can emit the therapeutic ultrasound with a frequency of 1.1 MHz.

The sample 4 is held on the focus of the transducer 7 by the ultrasound diagnostic probe for phase change monitoring 8. The medical ultrasound scanner 9 emits the phase-change ultrasound for about 1 millisecond, and then, irradiates the acoustic cavitation ultrasound for 5 seconds from the ultrasound transducer 7 by using the electric signal generator 10 for the phase-change waveform and the acoustic cavitation and the amplifier 11, while acquiring the echo signal (reflection wave of the phase-change detection ultrasound) by use of the transducer 7, and acquiring an acoustic signal from the sample 4 by use of an underwater microphone 12. A numeral 13 denotes an oscilloscope connected to the underwater microphone 12.

The phase-change ultrasound and the acoustic ultrasound (therapeutic ultrasound) are exposed in such a manner that the intensity of the phase-change ultrasound is fixed to be 750 W/cm$^2$, and the intensity of the acoustic ultrasound is changed from 0 to 600 W/cm$^2$, and a value (relative echo signal change) obtained by subtracting an average value of the echo signals on the focus of the ultrasound in 5 seconds during the exposure of the acoustic cavitation ultrasound from a value before the exposure of the ultrasound, and an average value (relative sub-harmonic intensity) of signals with 0.55 MHz in 5 seconds during the exposure of the acoustic cavitation are calculated. The calculated values are defined respectively as an index of the change on the ultrasound image and an index of a degree of the generation of cavitation. The experiment was carried out with phase-change nanodroplet and without phase-change nanodroplet. In the experiment with the phase-change nanodroplet, dispersion liquid prepared by a preparation method described below was used as being diluted to 1/100.

Next, the preparation method of nanoparticles will briefly be described. Components described below were added together, and 20 ml of distilled water was slowly added, and homogenized for 1 minute at ice temperature with 9500 rpm in a homogenizer ULTRA-TURRAX T25 (Janke & Knukel, Staufen Germany).

| | |
|---|---|
| Glycelol | 2.0 g |
| α-tocopherol | 0.02 g |
| Cholesterol | 0.1 g |
| Lecitin | 1.0 g |
| Perfluoropentane | 0.1 g |
| Perfluoroheptane | 0.1 g |

Emulsion prepared by the homogenization underwent a high-pressure emulsification process for 2 minutes under 20 MPa in a homogenizer Emulsiflex—C5 (Avestin, Ottawa Canada), and was filtered by a membrane filter of 0.4 micron. According to the process described above, almost clear microemulsion was prepared. It was confirmed by a dynamic light-scattering particle size distribution measuring device LB-550 (HOLIBA Ltd., Tokyo) that 98% or more of the prepared microemulsion had a diameter of 200 nm or less.

Figure 7A:
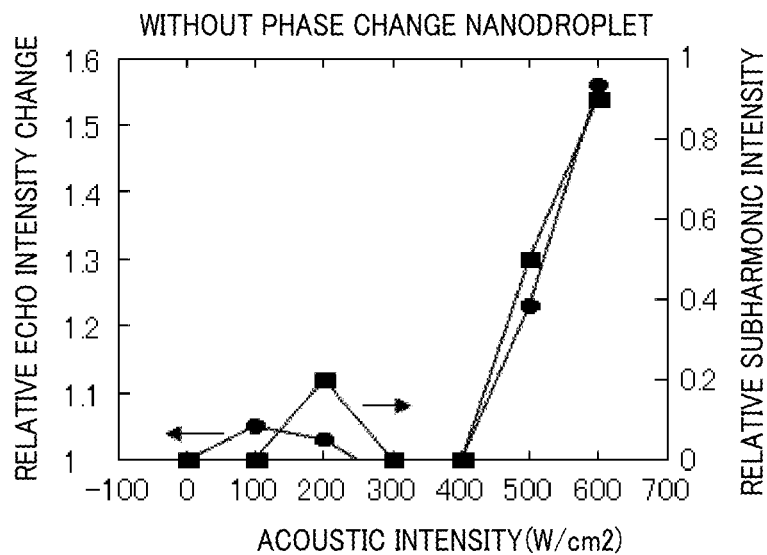
FIG. 7A is a view illustrating a result (a) in the experiment 1 illustrated in FIG. 6.
Figure 7B:
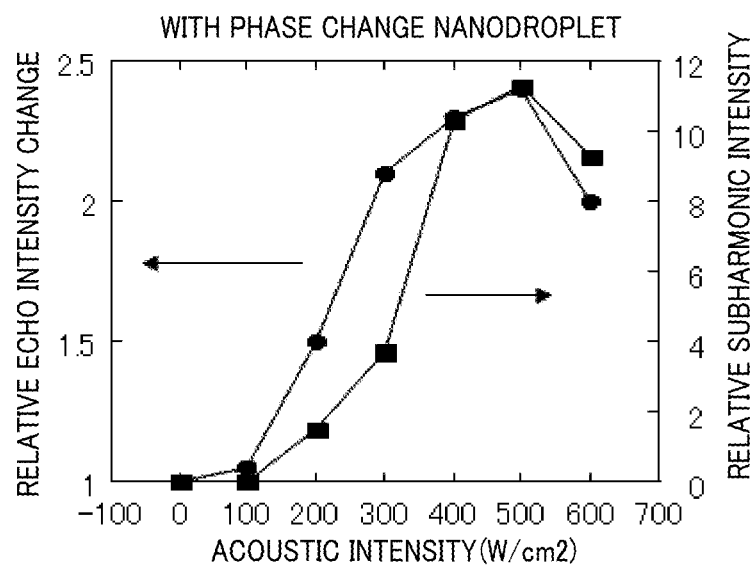
FIG. 7B is a view illustrating a result (b) in the experiment 1 illustrated in FIG. 6.
Figure 7C:
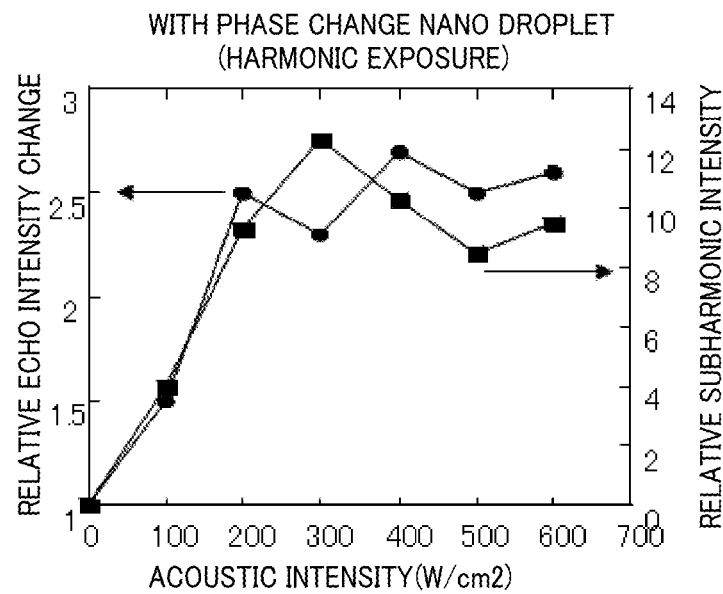
FIG. 7C is a view illustrating a result (c) in the experiment 1 illustrated in FIG. 6.

FIGS. 7A, 7B, and 7C are views illustrating one example of the result of the experiment. In these figures, an abscissa axis indicates the intensity of the ultrasound for generating the acoustic cavitation, a left ordinate axis indicates the relative echo intensity, and a right ordinate axis indicates the relative sub-harmonics intensity.

FIG. 7A illustrates the result when the phase-change nanodroplet is not contained, and FIG. 7B illustrates the result when the phase-change nanodroplet is contained. FIG. 7C illustrates the result when the phase-change nanodroplet is contained, and ultrasound with 3.3 MHz that is third harmonics is emitted for 30 microseconds at an interval of 20 ms with an intensity of 2 kW/cm$^2$ during the exposure of the ultrasound for inducing the acoustic cavitation. In any cases, sub-harmonic is generated, and there is a change in the echo signal observed almost simultaneously with the induction of the acoustic cavitation, whereby it is apparent that the induction of the acoustic cavitation can be confirmed through the measurement of the change in the echo signal. The similar result was confirmed, even when the frequency of the therapeutic ultrasound was changed to 0.5 MHz, 1.5 MHz, and 2.0 MHz. In FIG. 7C, the echo signal and the intensity of the sub-harmonic increase at the intensity of the ultrasound lower than that in FIG. 7B, and the same effect was obtained when the third harmonic was emitted by changing the intensity to 1 to 5 kW/cm$^2$ at an interval of 1 to 100 ms for 10 to 10000 microseconds.

Figure 17A:
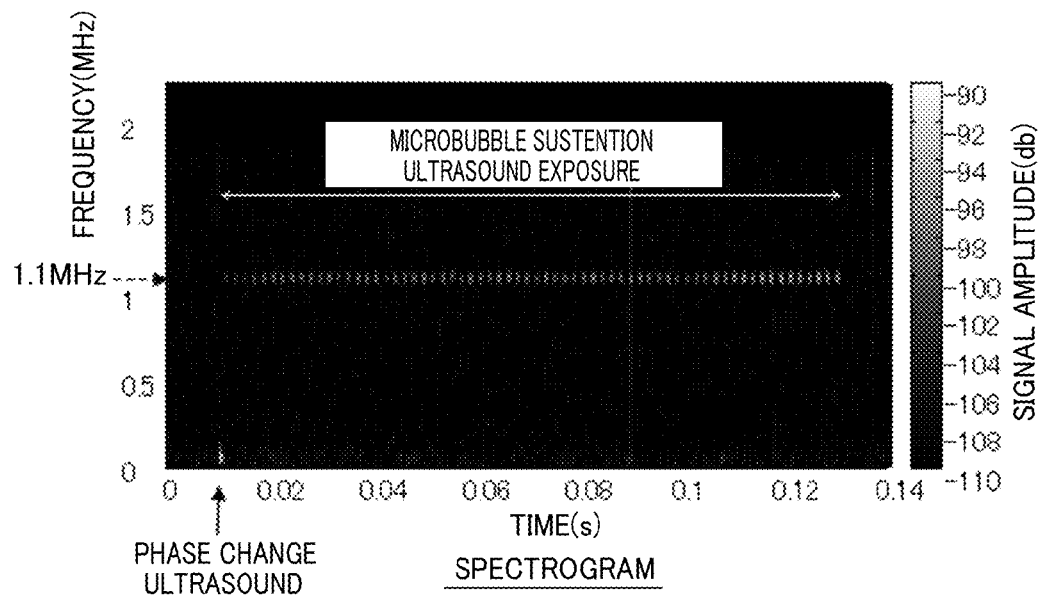
FIG. 17A is a view illustrating an effect of ultrasound for microbubble sustention according to the first embodiment.
Figure 17B:
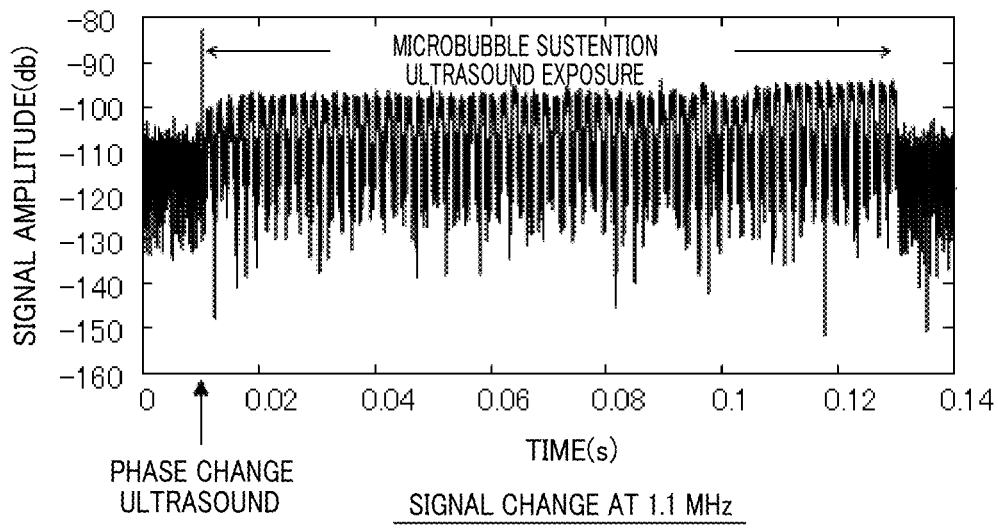
FIG. 17B is a view illustrating the effect of ultrasound for microbubble sustention according to the first embodiment.

Next, the effect of the microbubble sustention ultrasound in the present embodiment has been studied. FIGS. 17A and 17B show one example of the result. The result is obtained in such a manner that the experimental system same as the study whose result is shown in FIGS. 7A to 7C is used, the ultrasound is emitted with 3.3 MHz, 2 kW/cm$^2$, and 3 microseconds by use of the phase-change nanodroplet for the phase change, then, the microbubble sustention ultrasound with 1.1 MHz and 0.72 kW/cm$^2$ is emitted N times (N is a natural number of 1 or more) in a pulse form in which the exposure is ON in 1 millisecond and OFF in 1 millisecond, in order to perform the amplitude modulation to the microbubble sustention ultrasound, and the spectrogram obtained when the microbubble sustention ultrasound is emitted for 0.12 second and a temporal change of the frequency component (1.1 MHz) of the microbubble sustention ultrasound in the spectrogram are extracted. As illustrated in FIGS. 17A and 17B, the intensity of the ultrasound echo signal from the microbubbles fluctuates in synchronism with the amplitude modulation, so that it is found that the bubble echo signal from the microbubbles can be observed by the exposure of the microbubble sustention ultrasound.

Figure 18:
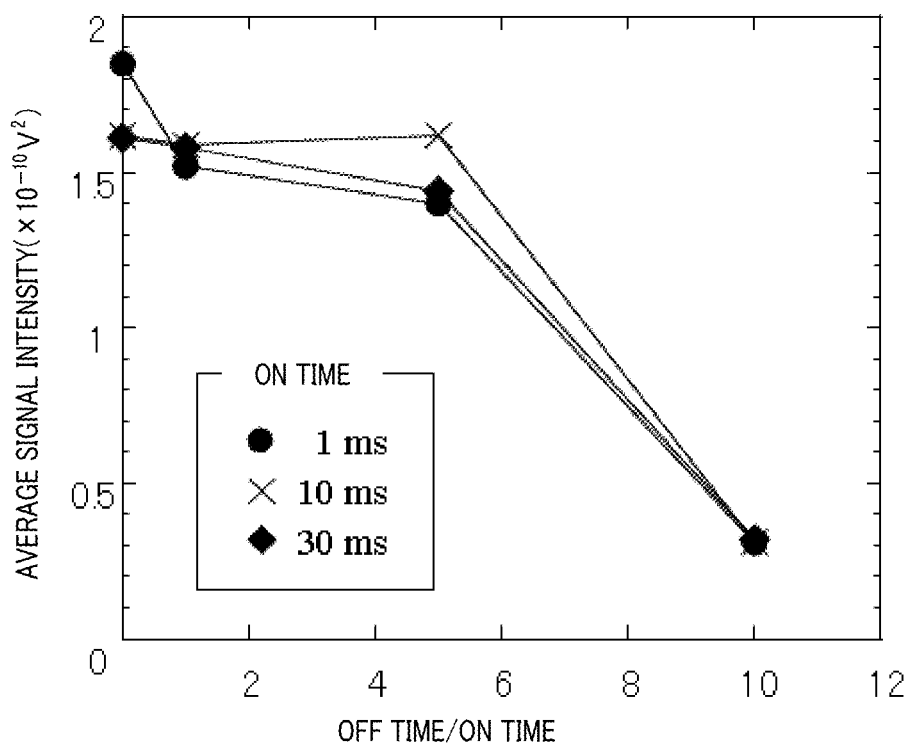
FIG. 18 is a view illustrating an effect of an exposure of ultrasound for microbubble sustention according to the first embodiment.

Based upon this result, the similar experiment is carried out with ON of x millisecond and OFF of y millisecond (x: 1, 10, 30 y: x×1, x×5, x×10), and FIG. 18 shows the result in which the maximum signal values in 1.1 MHz during the exposure of the microbubble sustention ultrasound are plotted. It is found that the microbubbles can be sustained in each ON-time, even if the OFF-time five times the ON-time is set. The similar result was obtained, when the frequency of the phase-change ultrasound was changed within the range of 0.75 to 5 MHz and the intensity thereof was changed within the range of 0.5 to 5 kW/cm$^2$, and the frequency of the microbubble sustention ultrasound was changed within the range of 0.5 to 2 MHz.

As described above, since the induction of the acoustic cavitation could be confirmed, and the effect of the microbubble sustention ultrasound could be verified, the experiment of the treatment of an actual tumor as in an experiment 2 was carried out next.

2) Experiment 2

Figure 8:
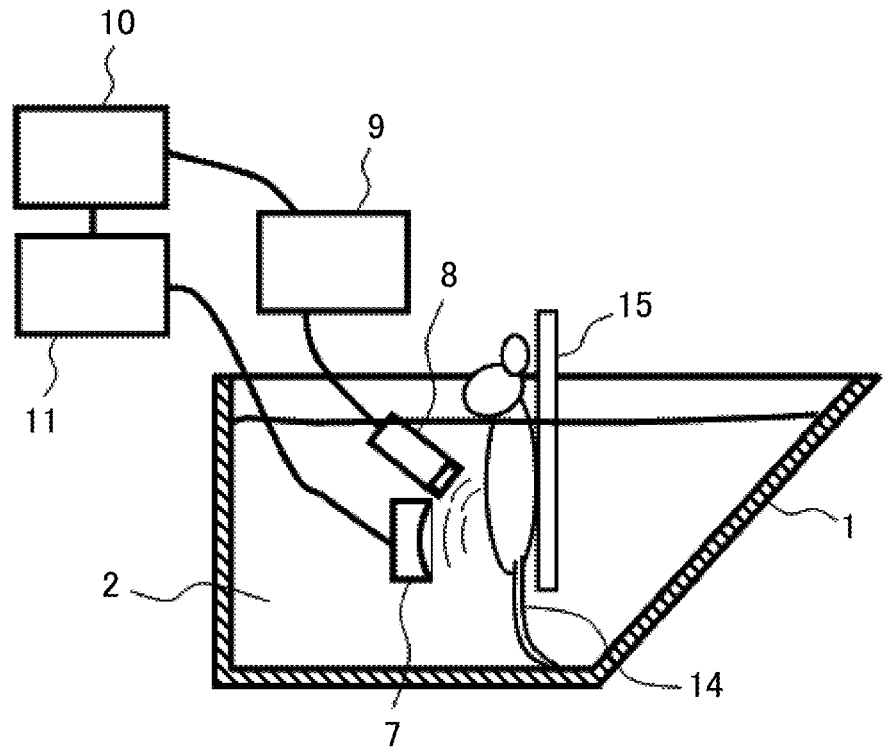
FIG. 8 is a view illustrating an example of a configuration of a device in an experimental system in an experiment 2 using a mouse tumor according to the first embodiment.

Relationship (Mouse Tumor) Between Induction of Acoustic Cavitation and Change in Intensity of Echo Signal Due to Exposure of Ultrasound In this experiment, phase-change nanodroplet was intravenously injected to a mouse, to which an experimental tumor of Colon 26 was transplanted under the skin, and the change in the intensity of the relative echo signal upon inducing the acoustic cavitation was checked by using an experimental system illustrated in FIG. 8. Basically, the sample in FIG. 6 was replaced to an anesthetized mouse 14.

In FIG. 8, the mouse 14 (under anesthesia) to which the phase-change nanodroplet prepared by the same process as in the experiment 1 was intravenously injected in an amount of 0.1 ml was held in water by use of the mouse holder 15 in a state in which degassed water 2 maintained at 37 degree Celsius was filled in the plastic water tank 1. The focused ultrasound transducer 7 for the phase change of the sample and cavitation induction (for therapy) has a diameter 40 mm, and f-number of 1, and can emit the therapeutic ultrasound with a frequency of 1.1 MHz. The mouse 14 is held on the focus of the transducer 7 by the ultrasound diagnostic probe for phase change monitoring 8. The medical ultrasound scanner 9 emits the phase-change ultrasound for about 1 millisecond, and then, emits the acoustic cavitation (therapeutic) ultrasound for 5 seconds from the ultrasound transducer 7 by using the wave generator 10 for a phase-change waveform and an acoustic cavitation and the amplifier 11, while acquiring the echo signal (before the phase change) by use of the transducer 7. The intensity of the phase-change ultrasound is fixed to 750 W/cm$^2$, and the intensity of the acoustic cavitation ultrasound is set to 500 W/cm$^2$. A value (relative echo signal change) obtained by subtracting the average value of the echo signals during the exposure of the ultrasound from the average value of the echo signals before the exposure of the ultrasound was calculated on the focus, on an outline of the focus by 3 pixels, and a non-focus apart from the focus by 15 pixels, respectively, and the obtained values were defined as an index of a change of the ultrasound image.

Figure 9A:
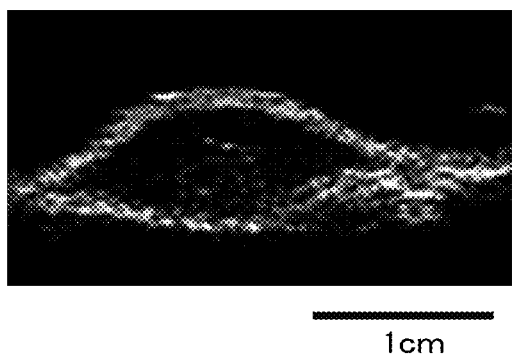
FIG. 9A is a view illustrating an ultrasound diagnostic image of the tumor as a result of the experiment 2 in FIG. 8.
Figure 9B:
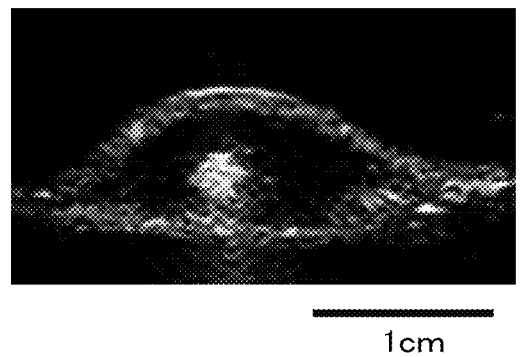
FIG. 9B is a view illustrating an ultrasound diagnostic image of the tumor as a result of the experiment 2 in FIG. 8.
Figure 9C:
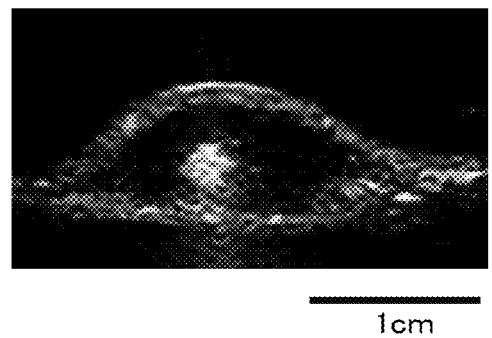
FIG. 9C is a view illustrating an ultrasound diagnostic image of the tumor as a result of the experiment 2 in FIG. 8.
Figure 9D:
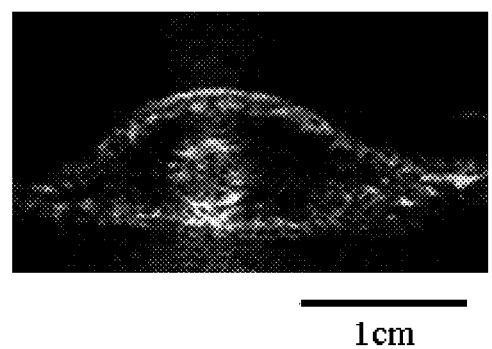
FIG. 9D is a view illustrating an ultrasound diagnostic image of the tumor as a result of the experiment 2 in FIG. 8.

FIGS. 9A to 9D and FIG. 10 are views illustrating one example of the result of the experiment. FIGS. 9A to 9D are ultrasound images of the mouse tumor in the present experiment, each illustrating the image before the phase-change ultrasound and the ultrasound for inducing the acoustic cavitation (for therapy) are emitted, the image after the exposure of the phase-change ultrasound, the image after the exposure of the ultrasound for inducing g the acoustic cavitation for 5 seconds, and the image after the exposure of the ultrasound for inducing the acoustic cavitation for 15 seconds, respectively. Although the microbubbles are generated on the focus region due to the phase change, so that the brightness increases, and the brightness change is continued because of the exposure of the ultrasound for inducing the acoustic cavitation, it is found that the brightness decreases after 15 seconds as illustrated in FIG. 9D.

Figure 10:
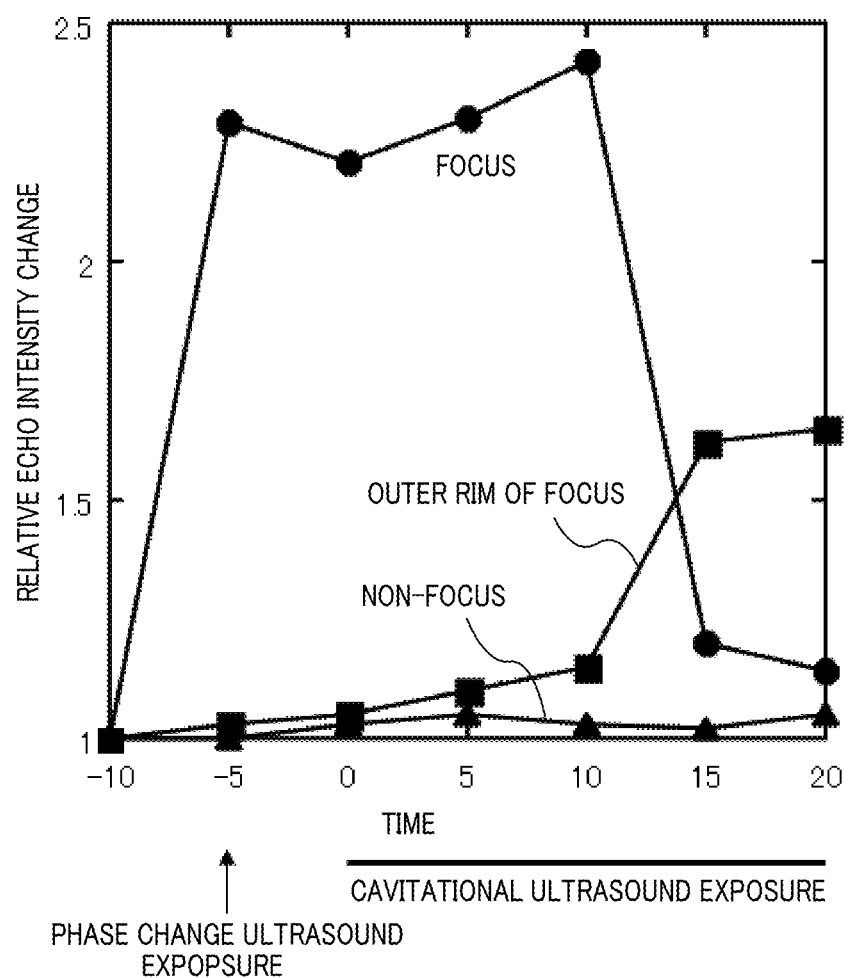
FIG. 10 is a view illustrating a temporal change of the echo signal as a result of the experiment 2 in FIG. 8.

FIG. 10 is a graph in which the echo signals, which are the bases for obtaining the result in FIG. 9, are plotted with time. It is apparent from FIG. 10 that the echo signals on the focus are reduced and the signals on the outline of the focus increase during the period of 10 seconds to 15 seconds after the exposure of the ultrasound for inducing the acoustic cavitation. It is found from the tissue observation after the exposure of the ultrasound that the tissue destruction (dissolution) progresses on the focus, and thermal coagulation occurs on the outline of the focus.

Consequently, when the acoustic cavitation is induced by the combination of the phase-change nanodroplet and the ultrasound, it is found that the tissue destruction (dissolution) progresses on the focus, and the thermal coagulation occurs on the outline of the focus, each phenomenon respectively causing the reduction in the intensity of the ultrasound echo signal and the increase in the intensity thereof.

3) Experiment 3

Induction (Mouse Tumor) of Acoustic Cavitation Under Image Monitoring

In the experiment 3, how the change on the echo signal caused by the induction of the acoustic cavitation under the coexistence of the phase-change nanodroplet is involved with the therapeutic effect is checked by using the experimental system illustrated in FIG. 8, wherein the change has been verified by the experiment 2. In order to check this relationship, the phase-change ultrasound and the ultrasound for inducing the acoustic cavitation were emitted, wherein the position is changed in order that the focuses of these ultrasounds were located on almost the whole area of the tumor having a diameter of about 1 cm, and with this state, the change in the diameter of the tumor was checked.

In the case where the phase-change nanodroplet was not used, the ultrasound was irradiated for 30 seconds for one portion. When the phase-change nanodroplet was administered, the exposure of the ultrasound was stopped at the time when the ultrasound echo signal became a half or less on each region. The average time required to reduce the ultrasound echo signal to a half was about 13 minutes after the exposure of the ultrasound for inducing the acoustic cavitation.

Figure 11:
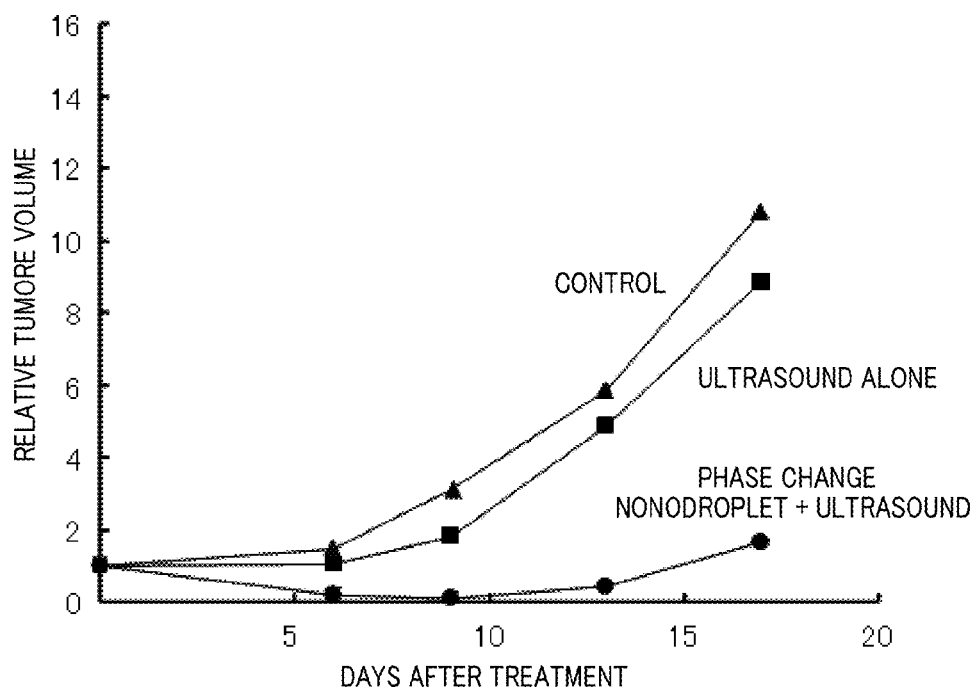
FIG. 11 is a view illustrating a growth curve of the tumor as a result of an experiment 3 according to the first embodiment.

FIG. 11 is a view illustrating one example of the result of the experiment 3. In FIG. 11, an abscissa axis indicates elapsed days after the exposure of the ultrasound, while an ordinate axis indicates a relative tumor volume calculated by measuring the diameter of the tumor with a slide gauge, on the assumption of a spheroid. There is little difference between the case where the ultrasound was emitted alone for a long period such as 30 seconds and the comparative experiment. However, the effect of reducing the volume of the tumor was dominantly observed in a group in which the ultrasound was emitted for 10 seconds and the phase-change nanodroplet was administered. From this result, it is apparent that the ultrasound sufficient for the treatment can be emitted by the process in which the acoustic cavitation is induced under the administration of the phase-change nanodroplet, and the treatment is finished at the time when the echo signal is reduced upon the exposure.

The same effect was confirmed even when the frequency of the therapeutic ultrasound was changed to 0.5, 1.5, and 2.0 MHz. It is understood from the result that the ultrasound sufficient for the treatment can be emitted by inducing the acoustic cavitation under the administration of the phase-change nanodroplet, and by monitoring this process by the medical diagnostic scanner.

CONCLUSION

In the above-mentioned embodiments, the ultrasound contrast agent, which is liquid upon administering to a living body, and which causes a phase change by the exposure of the ultrasound to become gas, is administered to the living body. The phase-change ultrasound (it does not necessarily have low frequency) is emitted to the therapy region of the living body, so as to cause the phase change in the contrast agent. Thereafter, the therapeutic ultrasound (low-frequency ultrasound with 0.5 to 2.5 MHz) is emitted to the therapy region to induce the cavitation. The echo signal (Ith) is acquired from the therapy region which is exposed to the therapeutic ultrasound, and when the intensity of the signal is larger than the therapeutic threshold value (ICpost−Iref(th)), it is determined that the therapy is completed.

Specifically, it may be determined that the therapy is completed, when the relative signal intensity of the echo signal intensity ICpost after the phase change and the echo signal intensity Ith from the therapy region becomes smaller than the threshold value Iref(th). More specifically, it is determined that the therapy is completed, when the intensity of the echo signal becomes ½ or less of the intensity of the echo signal upon the start of the exposure of the therapeutic ultrasound (start of the therapy). With this, the exposure of the ultrasound can be stopped at the time when the sufficient therapeutic effect is obtained. Therefore, the therapy can safely be done without the insufficient exposure of the ultrasound or without the excessive exposure of the ultrasound.

In addition, the region where the therapy is determined to be completed may be displayed on a display unit as the treated region where the therapy has already been completed. Thus, the user can visually find the completion of the therapy.

Not only the echo signal (therapy echo signal) from the therapy region (focus) but also the echo signal (outline echo signal) in the vicinity of the outline of the therapy region are acquired. When the intensity of the therapy echo signal is larger than the therapy threshold value, and the intensity of the outline echo signal is smaller than the threshold value for determining the peripheral coagulation (ICpost−Iref(th_lim)), the therapy t is determined to be completed. More specifically, the intensity of the echo signal on the therapy region becomes ½ or less of the intensity of the echo signal upon the start of the exposure of the therapeutic ultrasound (start of the therapy) (i.e., when the relative echo signal on the therapy region becomes ½ or less), and when the intensity of the echo signal on the outline becomes 1.5 times or more the intensity of the echo signal upon the start of the therapy (i.e., when the relative echo signal on the outline becomes 1.5 times or more), it is determined that the therapy is completed.

With this process, the therapy region can be contained. Therefore, the ultrasound apparatus for diagnosis and therapy can be realized, the apparatus being capable of preventing the situation in which, even if a part of the tumor is not treated and remains, the remaining tumor scatters and metastasizes to other regions of the target to be exposed, such as the living body.

INDUSTRIAL APPLICABILITY

The present invention is useful to an ultrasound apparatus for diagnosis and therapy, particularly to an ultrasound apparatus for diagnosis and therapy using a phase-change ultrasound contrast agent and ultrasound in combination with each other.

REFERENCE SINGS LIST

1 . . . Plastic water tank
2 . . . Degassed water maintained at 37 degree Celsius
3 . . . Sample containing tube
4 . . . Sample
5 . . . Clip for fixing edge of tube
6 . . . Sample holder
7 . . . Focused ultrasound transducer for phase change of sample and cavitation induction
8 . . . Ultrasound diagnostic probe for phase change monitoring
9 . . . Medical ultrasound scanner
10 . . . Wave generator
11 . . . Amplifier
12 . . . Underwater microphone
13 . . . Oscilloscope
14 . . . Anesthetized mouse
15 . . . Mouse holder
16 . . . Therapy target region
17 . . . Acoustic coupling media
18 . . . Phase-change ultrasound transmit unit
19 . . . Phase-change detection ultrasound transmit unit
20 . . . Therapeutic ultrasound transmit unit
21 . . . Phase-change ultrasound control unit
22 . . . Ultrasound control unit for quantification of phase change
23 . . . Therapeutic ultrasound control unit
24 . . . Signal processing unit for quantification of phase change
25 . . . Signal processing unit for therapy monitoring
26 . . . Central control unit
27 . . . Image processing unit
28 . . . Input and display unit
29 . . . Ultrasound transmit unit for microbubble sustention
30 . . . Control unit for microbubble sustention
31 . . . Outer piezoelectric element of ultrasound exposure apparatus
32 . . . Inner piezoelectric element of ultrasound exposure apparatus
190 . . . Ultrasound exposure apparatus

The invention claimed is:
1. An ultrasound apparatus for diagnosis and therapy that emits ultrasound to a predetermined region of a target to be exposed, for performing an ultrasound diagnosis and therapy, the apparatus comprising:
a phase-change ultrasound transmit unit that emits phase-change ultrasound to the predetermined region to which an ultrasound contrast agent, which causes a phase-change due to an exposure of ultrasound to become bubbles, is administered;
an ultrasound transmit unit for bubble sustention that emits ultrasound for bubble sustention for sustaining the generated bubbles to the predetermined region;

a therapeutic ultrasound transmit unit that emits therapeutic ultrasound to a therapy region of the predetermined region; and a control unit that controls the exposure of ultrasounds from the phase-change ultrasound transmit unit, the ultrasound transmit unit for bubble sustention, and the therapeutic ultrasound transmit unit, wherein:

a common ultrasound transmit unit is commonly used for the phase-change ultrasound transmit unit, the ultrasound transmit unit for bubble sustention and the therapeutic ultrasound transmit unit;

the control unit controls to emit the phase-change ultrasound, the ultrasound for bubble sustention, and the therapeutic ultrasound, sequentially via time-sharing, and controls the ultrasound transmit unit to vary a size of a focus region in the time-sharing, so that the phase-change ultrasound is emitted within less than a whole range to which the therapeutic ultrasound is emitted, and the ultrasound for bubble sustention emitted into the whole range to which the therapeutic ultrasound is emitted, so that the ultrasound for bubble sustention has a focus region which is wider in range than a focus region of the phase-change ultrasound; and the control unit detects a bubble echo signal from the predetermined region, and after confirming that the contrast agent is present in the therapy region, the control unit controls such that the therapeutic ultrasound is emitted to the predetermined region in a state in which the bubbles are generated and sustained on the predetermined region.

2. The ultrasound apparatus for diagnosis and therapy according to claim 1, further comprising:

a display unit that displays an image of the predetermined region of the target to be exposed; and an image processing unit that generates an image, which is to be displayed on the display unit, based upon the bubble echo signal, wherein the image processing unit performs an image process such that a portion of the predetermined region where the bubbles are sustained is displayed onto the display unit.

3. The ultrasound apparatus for diagnosis and therapy according to claim 1, wherein the therapeutic ultrasound has a frequency of 0.5 to 2.5 MHz.

4. The ultrasound apparatus for diagnosis and therapy according to claim 1, wherein the control unit controls to apply amplitude modulation to the ultrasound for bubble sustention that is emitted from the ultrasound transmit unit for bubble sustention, and detects that an intensity of the bubble echo signal fluctuates in synchronism with the amplitude modulation.

5. The ultrasound apparatus for diagnosis and therapy according to claim 1, wherein the control unit controls the exposure of the ultrasound, while shifting a focal position, in order that a temporal mean acoustic intensity of the ultrasound emitted to each position of the predetermined region becomes about 50 to 500 W/cm$^2$.

6. The ultrasound apparatus for diagnosis and therapy according to claim 1, wherein the control unit controls to emit the phase-change ultrasound to the predetermined region from the phase-change ultrasound transmit unit, and to emit the ultrasound for bubble sustention N times (N is a natural number of 1 or more) to the predetermined region from the ultrasound transmit unit for bubble sustention.

7. The ultrasound apparatus for diagnosis and therapy according to claim 1, wherein the phase-change ultrasound transmit unit, the ultrasound transmit unit for bubble sustention, and the therapeutic ultrasound transmit unit are composed of one ultrasound exposure apparatus.

8. The ultrasound apparatus for diagnosis and therapy according to claim 7, wherein the ultrasound exposure apparatus includes plural piezoelectric elements arranged concentrically on a concave inner surface.

9. The ultrasound apparatus for diagnosis and therapy according to claim 8, wherein the plural piezoelectric elements arranged concentrically on the ultrasound exposure apparatus are divided into plural outer piezoelectric elements and plural inner piezoelectric elements.

10. The ultrasound apparatus for diagnosis and therapy according to claim 9, wherein the control unit emits the ultrasound for bubble sustention by controlling the inner piezoelectric elements, and the control unit emits the therapeutic ultrasound by controlling the outer piezoelectric elements.

11. An ultrasound apparatus for diagnosis and therapy that emits ultrasound to a therapy region of a target to be exposed, for performing an ultrasound diagnosis and treatment, the apparatus comprising:

a phase-change ultrasound transmit unit that emits phase-change ultrasound to the therapy region to which an ultrasound contrast agent, which causes a phase-change due to an exposure of ultrasound to become bubbles, is administered;

an ultrasound transmit unit for bubble sustention that emits ultrasound for bubble sustention for sustaining the generated bubbles to the therapy region;

a therapeutic ultrasound transmit unit that emits therapeutic ultrasound to the therapy region;

a common ultrasound transmit unit is commonly used for the phase-change ultrasound transmit unit, the ultrasound transmit unit for bubble sustention and the therapeutic ultrasound transmit unit; and a control unit that controls the exposure of the phase-change ultrasound, the ultrasound for bubble sustention, and the therapeutic ultrasound, sequentially via time-sharing, and controls the ultrasound transmit unit to vary a size of a focus region in the time-sharing, so that the phase-change ultrasound is emitted within less than a whole range to which the therapeutic ultrasound is emitted, and the ultrasound for bubble sustention is emitted into the whole range to which the therapeutic ultrasound is emitted, so that the ultrasound for bubble sustention has a focus region which is wider in range than a focus region of the phase-change ultrasound.

12. The ultrasound apparatus for diagnosis and therapy according to claim 11, wherein the control unit controls to emit the therapeutic ultrasound to the therapy region, when determining that the bubbles are sustained on the therapy region.

13. The ultrasound apparatus for diagnosis and therapy according to claim 11, further comprising:

a display unit; and an image processing unit that executes a process of displaying an ultrasound image of the target to be exposed on the display unit, wherein the image processing unit performs a process such that a portion of the therapy region determined by the control unit where the bubbles are sustained, is displayed onto the display unit.

14. The ultrasound apparatus for diagnosis and therapy according to claim 11,
wherein the therapeutic ultrasound is low-frequency ultrasound having a frequency of 0.5 to 2.5 MHz.

15. The ultrasound apparatus for diagnosis and therapy according to claim 11,
wherein the control unit performs amplitude modulation of an intensity of the ultrasound for bubble sustention, and detects that an intensity of the bubble echo signal fluctuates in synchronism with the intensity of the ultrasound for bubble sustention.

16. The ultrasound apparatus for diagnosis and therapy according to claim 11,
wherein the control unit controls the exposure of the ultrasound, while shifting a focal position of the therapeutic ultrasound, in order that a temporal mean acoustic intensity on each position of the therapy region, becomes about 50 to 500 W/cm$^2$ due to the exposure of the therapeutic ultrasound.

17. The ultrasound apparatus for diagnosis and therapy according to claim 11,
wherein the control unit controls to emit the phase-change ultrasound to the therapy region from the phase-change ultrasound transmit unit, and to emit the ultrasound for bubble sustention N times (N is a natural number of 1 or more) to the therapy region from the ultrasound transmit unit for bubble sustention.

18. The ultrasound apparatus for diagnosis and therapy according to claim 11,
wherein the control unit controls the exposure of the phase-change ultrasound, the ultrasound for bubble sustention, and the therapeutic ultrasound based upon a focus, set beforehand, of ultrasound covering the therapy region and an order of focus moving.

19. The ultrasound apparatus for diagnosis and therapy according to claim 12,
wherein the control unit controls to divide the therapy region, to acquire a bubble echo signal from each of the divided therapy regions, and to emit the therapeutic ultrasound to each of the divided therapy regions, when determining that the bubbles are sustained on the therapy region.

20. An ultrasound apparatus for diagnosis and therapy that emits ultrasound to a predetermined region of a target to be exposed, for performing an ultrasound diagnosis and therapy, the apparatus comprising:
a phase-change ultrasound transmit unit that emits phase-change ultrasound to the predetermined region to which an ultrasound contrast agent, which causes a phase-change due to an exposure of ultrasound to become bubbles, is administered;
an ultrasound transmit unit for bubble sustention that emits ultrasound for bubble sustention for sustaining the generated bubbles to the predetermined region;
a therapeutic ultrasound transmit unit that emits therapeutic ultrasound to a therapy region of the predetermined region; and
a control unit that controls the exposure of ultrasounds from the phase-change ultrasound transmit unit, the ultrasound transmit unit for bubble sustention, and the therapeutic ultrasound transmit unit,
wherein:
the control unit controls to emit the phase-change ultrasound, the ultrasound for bubble sustention, and the therapeutic ultrasound, sequentially via time-sharing, and controls the ultrasound transmit unit to vary a size of a focus region in the time-sharing, so that the phase-change ultrasound is emitted within less than a whole range to which the ultrasound for bubble sustention is emitted, and so that the ultrasound for bubble sustention has a focus region which is wider in range than a focus region of the phase-change ultrasound; and
the control unit detects a bubble echo signal from the predetermined region, and after confirming that the contrast agent is present in the therapy region, the control unit controls such that the therapeutic ultrasound is emitted to the predetermined region in a state in which the bubbles are generated and sustained on the predetermined region.

* * * * *